United States Patent
Hu et al.

(10) Patent No.: US 8,738,114 B2
(45) Date of Patent: May 27, 2014

(54) SYSTEMS AND METHODS FOR MEASURING AND MODELING IN VIVO MANGANESE ION TRANSPORT IN A SUBJECT

(75) Inventors: Tom Chih-Chuang Hu, Rockville, MD (US); Benjamin J. Waghorn, Orlando, FL (US); Nathan E. Yanasak, Crawfordville, GA (US)

(73) Assignee: Celtrast LLC, Augusta, GA (US)

(*) Notice: Subject to any disclaimer, the term of this patent is extended or adjusted under 35 U.S.C. 154(b) by 72 days.

(21) Appl. No.: 13/145,036

(22) PCT Filed: Feb. 9, 2010

(86) PCT No.: PCT/US2010/023641
§ 371 (c)(1),
(2), (4) Date: Oct. 4, 2011

(87) PCT Pub. No.: WO2010/093635
PCT Pub. Date: Aug. 19, 2010

(65) Prior Publication Data
US 2012/0123247 A1  May 17, 2012

Related U.S. Application Data

(60) Provisional application No. 61/207,284, filed on Feb. 10, 2009, provisional application No. 61/207,285, filed on Feb. 10, 2009.

(51) Int. Cl.
*A61B 5/05* (2006.01)
(52) U.S. Cl.
USPC .......................................... 600/420; 600/410
(58) Field of Classification Search
None
See application file for complete search history.

(56) References Cited

U.S. PATENT DOCUMENTS

| 6,846,641 B2 | 1/2005 | Wieloch et al. |
| 2002/0090341 A1 | 7/2002 | Watson et al. |

(Continued)

FOREIGN PATENT DOCUMENTS

| WO | 2007122553 | 11/2007 |
| WO | 2008093999 | 8/2008 |
| WO | 2010093635 | 8/2010 |

OTHER PUBLICATIONS

Skjold et al., An Apparent Unidirectional Influx Constant for Manganese as a Measure of Myocardial Calcium Channel Avtivity, Oct. 5. 2006, Journal of Magnetic Resonance Imaging, 24, p. 1047-1055.*
International Search Report dated Aug. 30, 2010 for international application No. PCT/US2010/023641.
Written Opinion and International Search Report of the International Searching Authority for PCT Application Serial No. PCT/US2009/038577 dated Jun. 16, 2009.

*Primary Examiner* — Unsu Jung
*Assistant Examiner* — Joel Lamprecht
(74) *Attorney, Agent, or Firm* — Gardner, Groff, Greenwald, & Villanueva, P.C.

(57) ABSTRACT

Described herein are systems and methods for quantitatively measuring manganese ion efflux in a subject. In general, the systems and methods compare imaging data from a subject taken over specific periods of time to pharmacokinetic models in order to measure manganese ion efflux rates from an organ in a subject. By understanding the specific location and rate of manganese ion efflux and influx from the organ, it is possible to more accurately correlate calcium ion activity. Calcium ion efflux is associated with a number of biological mechanisms in the subject, and the methods and systems described herein can be used as a diagnostic tool not only for monitoring calcium efflux in the subject but also aid in the treatment of diseases associated with changes in calcium ion efflux.

21 Claims, 12 Drawing Sheets

(56) References Cited

U.S. PATENT DOCUMENTS

| | | | |
|---|---|---|---|
| 2004/0096520 | A1 | 5/2004 | Nonotte et al. |
| 2004/0242994 | A1* | 12/2004 | Brady et al. .................. 600/420 |
| 2005/0136002 | A1* | 6/2005 | Fossheim et al. ............ 424/1.11 |
| 2005/0249667 | A1 | 11/2005 | Tuszynski et al. |
| 2006/0235292 | A1 | 10/2006 | Rongved et al. |
| 2007/0293436 | A1 | 12/2007 | Peterson et al. |
| 2008/0044827 | A1 | 2/2008 | Bogdanov et al. |
| 2008/0081021 | A1 | 4/2008 | Bilgen et al. |
| 2009/0246144 | A1 | 10/2009 | Hu et al. |
| 2010/0166667 | A1* | 7/2010 | Jynge et al. .................. 424/9.36 |

OTHER PUBLICATIONS

Dhalla NS, Pierce GN, Panagia V, Singal PK, Beamish RE. Calcium movements in relation to heart function. Basic Res Cardiol 1982; 77; 2: 117-139.

Caroni P, Carafoli E. An ATP-dependent $Ca^{2+}$-pumping system in dog heart sarcolemma. Nature 1980; 283; 5749: 765-767.

Bassani JW, Bassani RA, Bers DM. Relaxation in rabbit and rat cardiac cells: species-dependent differences in cellular mechanisms. J Physiol 1994; 476; 2: 279-293.

Varro A, Negretti N, Hester SB, Eisner DA. An estimate of the calcium content of the sarcoplasmic reticulum in rat ventricular myocytes. Pflugers Arch 1993; 423; 1-2: 158-160.

Antoons G, Mubagwa K, Nevelsteen I, Sipido KR. Mechanisms underlying the frequency dependence of contraction and $[Ca^{2+}]i$ transients in mouse ventricular myocytes. J Physiol 2002; 543; Pt 3: 889-898.

Houser SR, Piacentino V, 3rd, Weisser J. Abnormalities of calcium cycling in the hypertrophied and failing heart. J Mol Cell Cardiol 2000; 32; 9: 1595-1607.

Saini HK, Shao Q, Musat S, Takeda N, Tappia PS, Dhalla NS. Imidapril treatment improves the attenuated inotropic and intracellular calcium responses to ATP in heart failure due to myocardial infarction. Br J Pharmacol 2005; 144; 2: 202-211.

Zhang XQ, Musch TI, Zelis R, Cheung JY. Effects of impaired $Ca^{2+}$ homeostasis on contraction in postinfarction myocytes. J Appl Physiol 1999; 86; 3: 943-950.

Mendonca-Dias MH, Gaggelli E, Lauterbur PC. Paramagnetic contrast agents in nuclear magnetic resonance medical imaging. Semin Nucl Med 1983; 13; 4: 364-376.

Cory DA, Schwartzentruber DJ, Mock BH. Ingested manganese chloride as a contrast agent for magnetic resonance imaging. Magn Reson Imaging 1987; 5; 1: 65-70.

Anderson M. Mn ions pass through calcium channels. A possible explanation. J Gen Physiol 1983; 81; 6: 805-827.

Narita K, Kawasaki F, Kita H. Mn and Mg influxes through Ca channels of motor nerve terminals are prevented by verapamil in frogs. Brain Res 1990; 510; 2: 289-295.

Shibuya I, Douglas WW. Indications from Mn-quenching of Fura-2 fluorescence in melanotrophs that dopamine and baclofen close Ca channels that are spontaneously open but not those opened by high [K+]O; and that Cd preferentially blocks the latter. Cell Calcium 1993; 14; 1: 33-44.

Hu TC, Pautler RG, MacGowan GA, Koretsky AP. Manganese-enhanced MRI of mouse heart during changes in inotropy. Magn Reson Med 2001; 46; 5: 884-890.

Skjold A, Kristoffersen A, Vangberg TR, Haraldseth O, Jynge P, Larsson HB. An apparent unidirectional influx constant for manganese as a measure of myocardial calcium channel activity. J Magn Reson Imaging 2006; 24; 5: 1047-1055.

Takahashi K, Takahashi T, Suzuki T, Onishi M, Tanaka Y, Hamano-Takahashi A, Ota T, Kameo K, Matsuda T, Baba A. Protective effects of SEA0400, a novel and selective inhibitor of the Na+/Ca2+ exchanger, on myocardial ischemia-reperfusion injuries. Eur J Pharmacol 2003; 458; 1-2: 155-162.

Tani M, Neely JR. Role of intracellular Na+ in Ca2+ overload and depressed recovery of ventricular function of reperfused ischemic rat hearts. Possilbe involvement of H+-Na+ and Na+ -Ca2+ exchange. Circ. Res. 1989; 65(4): 1045-1056.

Kusuoka H, Camilion de Hurtado MC, Marban E. Role of sodium/calcium exchange in the mechanism of myocardial stunning: protective effect of reperfusion with high sodium solution. J. Am. Coll. Cardiol. 1993; 21(1): 240-248.

Yoshiyama M., Nakamura Y, Omura T, Hayashi T., Takagi Y, Hasegawa T., Nishioka H, Takeuchi K, Iwao H., Youshikawa J. Cardioprotective effect of SEA0400, a selective inhibitor of the Na+/Ca2+ exchanger, on myocardial ischemia-reperfusion injury in rats. J. Pharmacol. Sci. 2004; 95(2): 196-202.

Matsuda T, Arakawa N, Takuma K, Kishida Y, Kawasaki Y, Sakaue M, Takahashi K, Takahashi T, Suzuki T., Ota T, Hamano-Takahashi A, Onishi M, Tanaka Y, Kameo K, Baba A. SEA0400, a novel and selective inhibitor of the Na+-Ca2+ exchanger, attenuates reperfusion injury in the in vitro and in vivo cerbral ischemic models. J. Pharmacol. Exp. There. 2001; 298(1): 249-256.

Hu TC, Christian TF, Aletras AH, Taylor JL, Koretsky AP, Arai AE. Manganese enhanced magnetic resonance imaging of normal and ischemic canine heart. Magn Reson Med 2005; 54; 1: 196-200.

Frahm J, Haase A, Matthaei D. Rapid NMR imaging of dynamic processes using the FLASH technique. Magn Reson Med 1986; 3; 2: 321-327.

Chuang KH, Koretsky A. Improved neuronal tract tracing using manganese enhanced magnetic resonance imaging with fast T1 mapping. Magn Reson Med 2006; 55; 3: 604-611.

Loening AM, Gambhir SS. AMIDE: a free software tool for multimodality medical image analysis. Mol Imaging 2003; 2; 3: 131-137.

Webb AI, Weaver BM. The density of equine tissue at 37 degrees C. Res Vet Sci 1979; 26; 1: 71-75.

Nordhoy W, Anthonsen HW, Bruvold M, Brurok H, Skarra S, Krane J, Jynge P. Intracellular manganese ions provide strong T1 relaxation in rat myocardium. Magn Reson Med 2004; 52; 3: 506-514.

Lee C, Visen NS, Dhalla NS, Le HD, Isaac M, Choptiany P, Gross G, Omelchenko A, Matsuda T, Baba A, Takahashi K, Hnatowich M, Hryshko LV. Inhibitory profile of SEA0400 [2-[4-[(2,5-difluorophenyl)methoxy]phenoxy]-5-ethoxyaniline] assessed on the cardiac Na+-Ca2+ exchanger, NCX1.1. J Pharmacol Exp Ther 2004; 311; 2: 748-757.

Farkas AS, Acsai K, Nagy N, Toth A, Fulop F, Seprenyi G, Birinyi P, Nanasi PP, Forster T, Csanady M, Papp JG, Varro A, Farkas A. Na+/Ca2+ exchanger inhibition exerts a positive inotropic effect in the rat heart, but fails to influence the contractility of the rabbit heart. Br J Pharmacol 2008; 154; 1:93-104.

Waghorn et al., "Assessing manganese efflux using SEA0400 and cardiac T1-mapping manganese-enhanced MRI in a murine model", Wiley InterScience: 2009, NMR in Biomedicine, May 2009, www.interscience.wiley.com/journal/nbm.

Waghorn et al., "Monitoring dynamic alterations in calcium homeostasis by T1-weighted and T1-mapping cardiac manganese-enhanced MRI in a murine myocardial infarction model", NMR Biomed, 2008; 21; 1102-1111.

Rowland et al., "Clinical Pharmacokinetics: concepts and applications", Lippincott Williams & Wilkins, 1995, third edition, ISBN: 0-683-07404-0.

Saeed, "T1-relaxation kinetics of extracellurlar, intracellular and intravascular MR contrast agents in normal and cutely reperfused infarcted myocardium using echo-planar MR imaging", Eur. Radiol. 10, 2000, 310-318.

Tanaka, "Effect of SEA0400, a novel inhibitor of sodium-calcium exchanger on myocardial ionic currents", British Journal of Pharmacology, 2002, 135, 1096-1100.

Hu et al, "Simultaneous assessment of left-ventricular infarction size, function and tissue viability in a murine model of myocardial infarction by cardiac manganese-enhanced magnetic resonance imaging (MEMRI)", NMR Biomed, 2004, 17; 620-626.

Medina et al, "Na+/CA2+exchanger-mediated Mn2+-enhanced 1H2O MRI in hypoxic, perfused rat myocardium", Contrast Media Mol. Imaging, 2007, 2: 248-257.

* cited by examiner

US 8,738,114 B2

SYSTEMS AND METHODS FOR MEASURING AND MODELING IN VIVO MANGANESE ION TRANSPORT IN A SUBJECT

CROSS REFERENCE TO RELATED APPLICATION

This application claims priority to U.S. provisional application Ser. Nos. 61/207,284 and 61/207,285, both filed on Feb. 10, 2009, which are hereby incorporated by reference in their entireties for all of their teachings.

FIELD OF THE INVENTION

The present invention is directed generally to systems and methods for measuring and modeling in vivo manganese ion transport in a subject.

BACKGROUND

Intracellular calcium ($Ca^{2+}$) is the central regulator of cardiac contractility. A majority of $Ca^{2+}$ ions entering cardiac cells via L-type calcium channels induce calcium release from the sarcoplasmic reticulum (SR). The resultant increase in intracellular free calcium, $[Ca^{2+}]_i$, boosts the amount of $Ca^{2+}$ binding to the thin-filament protein troponin C, ultimately resulting in contraction. During relaxation, $Ca^{2+}$ is removed from the cytosol via one of four transporters: two extracellular transporters (the sodium-calcium exchanger, NCX, and plasma membrane $Ca^{2+}$-ATPase, PMCA), and two intracellular transporters (SR $Ca^{2+}$-ATPase and mitochondrial $Ca^{2+}$ uniporter). Previous attempts to estimate the relative contributions to $Ca^{2+}$ efflux have shown that the NCX is the dominant efflux mechanism.

In addition to the important role of $Ca^{2+}$ in the function of viable myoctyes, alterations in $Ca^{2+}$ handling, primarily via increases in $[Ca^{2+}]_i$, provide a major contribution to irreversible ischemic damage. Cell death can result from one of several mechanisms following elevations in $[Ca^{2+}]_i$. Examples of these mechanisms include protease activation, membrane rupture, cell contracture, and gap junction dysfunction. Protocols that selectively inhibit the NCX are useful for investigating the roles of the NCX and PMCA, and have been shown to have potential therapeutic effects during myocardial ischemic-reperfusion injuries. When the NCX works as a pathway for $Ca^{2+}$ entry, as it does during ischemia/reperfusion injury, the NCX inhibitor is expected to guard against $Ca^{2+}$ overloading. SEA0400, a selective and potent NCX inhibitor, has been shown to provide protection from cardiac ischemia/reperfusion injury and from myocardial stunning.

Despite the established importance of $Ca^{2+}$ for myocardial viability, no in vivo imaging technique exists to assess the $Ca^{2+}$ content or changes in $Ca^{2+}$ handling post-MI in the heart. Molecular contrast agent manganese ($Mn^{2+}$) has been used as a surrogate marker to assess intracellular $Ca^{2+}$ movement in vivo indirectly. $Mn^{2+}$ has an ionic radius and chemical properties comparable to $Ca^{2+}$, and is known to shorten the longitudinal magnetization relaxation time, $T_1$, observed during manganese-enhanced magnetic resonance imaging (MEMRI). Furthermore, $Mn^{2+}$ enters viable myocardial tissue via the L-type voltage-gated $Ca^{2+}$ channels. The methods described herein can be used as a diagnostic tool in the early detection of abnormal $Ca^{2+}$ handling in the myocardium, and for monitoring disease progression.

SUMMARY

Described herein are systems and methods for quantitatively measuring manganese ion efflux in a subject. In general, the systems and methods compare imaging data from a subject taken over specific periods of time to pharmacokinetic models in order to measure manganese ion efflux rates from an organ in a subject. By understanding the specific location and rate of manganese ion efflux and influx from the organ, it is possible to more accurately correlate calcium ion activity. Calcium ion efflux is associated with a number of biological mechanisms in the subject, and the methods and systems described herein can be used as a diagnostic tool not only for monitoring calcium efflux in the subject but also aid in the treatment of diseases associated with changes in calcium ion efflux.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION

Figure 1:
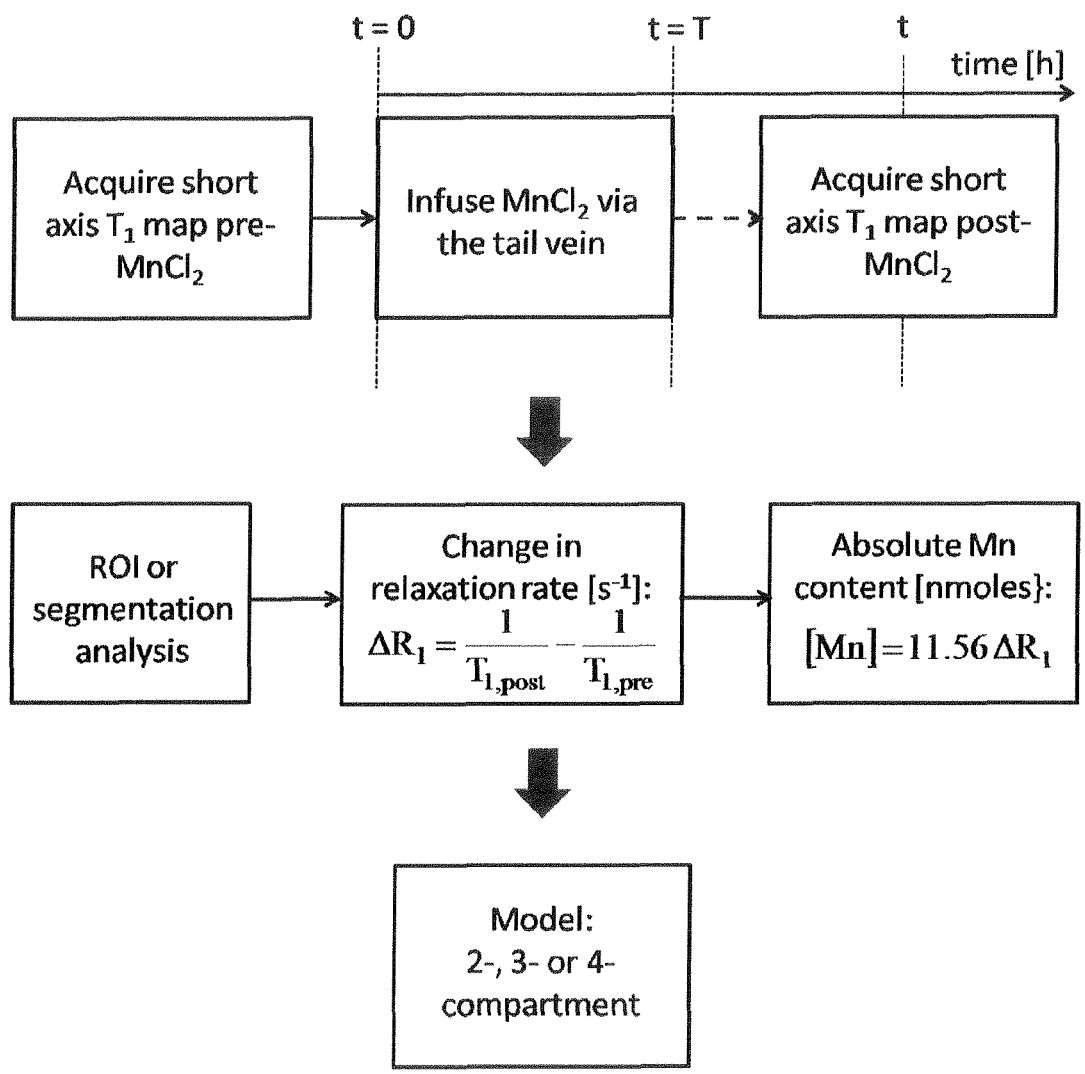
FIG. 1 shows a flow chart of the process of data acquisition and absolute Mn content calculation for the efflux studies leading to the modeling of Mn transport with either 2-, 3- or 4-compartment models.

The present invention may be understood more readily by reference to the following detailed description of the invention taken in connection with the accompanying drawing figures, which form a part of this disclosure. It is to be understood that this invention is not limited to the specific devices, compounds, compositions, methods, conditions, or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a cell" includes two or more cells, and the like.

"Optional" or "optionally" means that the subsequently described event or circumstance can or cannot occur, and that the description includes instances where the event or circumstance occurs and instances where it does not.

Described herein are systems and methods for detecting a change in manganese ion efflux and/or influx from an organ in a subject, the method comprising:
a. imaging the organ of the subject to obtain a baseline concentration of manganese ions in the organ;
b. administering to the subject a known concentration of a source of manganese ions;
c. imaging the organ of the subject after step (b) to obtain the concentration of manganese ions;
d. comparing the manganese ion concentration from step (c) to a standard pharmacokinetic model of a healthy organ at the same manganese ion concentration in step (b), wherein a deviation from the standard pharmacokinetic model indicates a change in manganese ion efflux and/or influx from the organ.

As will be described below in greater detail, a manganese containing compound can be used to qualitatively and quantitatively predict relative calcium efflux from a cell. A manganese ion ($Mn^{2+}$) has a comparable ionic radius and comparable chemical properties to that of a calcium ion ($Ca^{2+}$). Additionally, manganese ions shorten the proton magnetization $T_1$ relaxation time during manganese-enhanced magnetic resonance imaging (MEMRI). In the case of the heart, $Mn^{2+}$ enters viable myocardial tissue via the L-type voltage-gated $Ca^{2+}$ channels and accumulates in the excitable myocardial cells in an additive fashion. Without wishing to be bound by theory, it is theorized that the ability to measure $Mn^{2+}$ efflux in vivo using MEMRI as a quantitative imaging approach reflects actual myocardial $Ca^{2+}$ efflux.

Calcium ion effluxes within a cell or subject are often associated with abnormal cellular events which may lead to cellular damage within cell culture or a subject and to tissue damage in a subject. Depending on the abnormal cellular event, apoptosis may occur or in the alternative cellular and tissue necrosis may occur. An abnormal cellular event includes, for example, an ischemic event such as heart palpitations, a myocardial infarction, chest pain, shortness of breath, nausea, vomiting, sweating, anxiety, fatigue, atrial fibrillation, heart attack, cardiac arrest, heart failure, or any combination thereof.

Without wishing to be bound by theory, it is theorized that if the cells or tissues undergoing an ischemic event are assayed using the system and methods described herein shortly after the onset of an ischemic event, the magnitude of cellular damage and tissue damage may be reversed by the quick administration of appropriate therapeutic agents. Alternatively, if cellular damage and tissue damage cannot be reversed, the magnitude of cellular and tissue damage may be predicted and quantified.

The method begins with imaging an organ of interest in the subject in order to obtain a baseline concentration of manganese ions present in the organ. The relevance of obtaining the baseline concentration of manganese ion concentration will be addressed in detail below. In one aspect, the organ is imaged with an MRI machine. For example, the practitioner can use an MRI mapping technique, a manganese-enhanced MRI (MEMRI) mapping technique, or a combination thereof.

In one aspect, prior to the administration of the source of manganese ions, the organ can be imaged to produce an initial $T_1$ map. From the initial $T_1$ map, subsequent $T_1$ maps can be obtained over time after administration of a known concentration of manganese ions to generate temporal in vivo $\Delta R_1$ values. For example, temporal in vivo $\Delta R_1$ values can be calculated from manganese-enhanced MRI (MEMRI) $T_1$ maps as (post-$Mn^{2+}$ infusion $1/T_1$)–(pre-$Mn^{2+}$ infusion $1/T_1$). The temporal $\Delta R_1$ values can then be fit to a first order exponential decay using a least-square fitting technique with GraphPad Prism statistics software. Values of the exponential $\Delta R_1$ half-life are calculated from the exponential fit. To ascertain the relationship between the temporal response of $\Delta R_1$ post-$MnCl_2$ infusion and the absolute $Mn^{2+}$ concentration, tissue samples from the organ and/or blood can be analyzed ex vivo using analytical techniques such as, for example, ICP-MS. The Examples demonstrate this approach, where the following equation was used to determined for changes in $Mn^{2+}$ concentration (nmoles) relative to temporal in vivo $\Delta R_1$ values:

$$\text{Mn ion concentration[nmoles]} = 11.56 \cdot \Delta R_1 [\text{sec}^{-1}] \quad (12)$$

A flow chart summarizing the calculation of manganese concentration using $T_1$ mapping is provided in FIG. 1.

Figure 2:
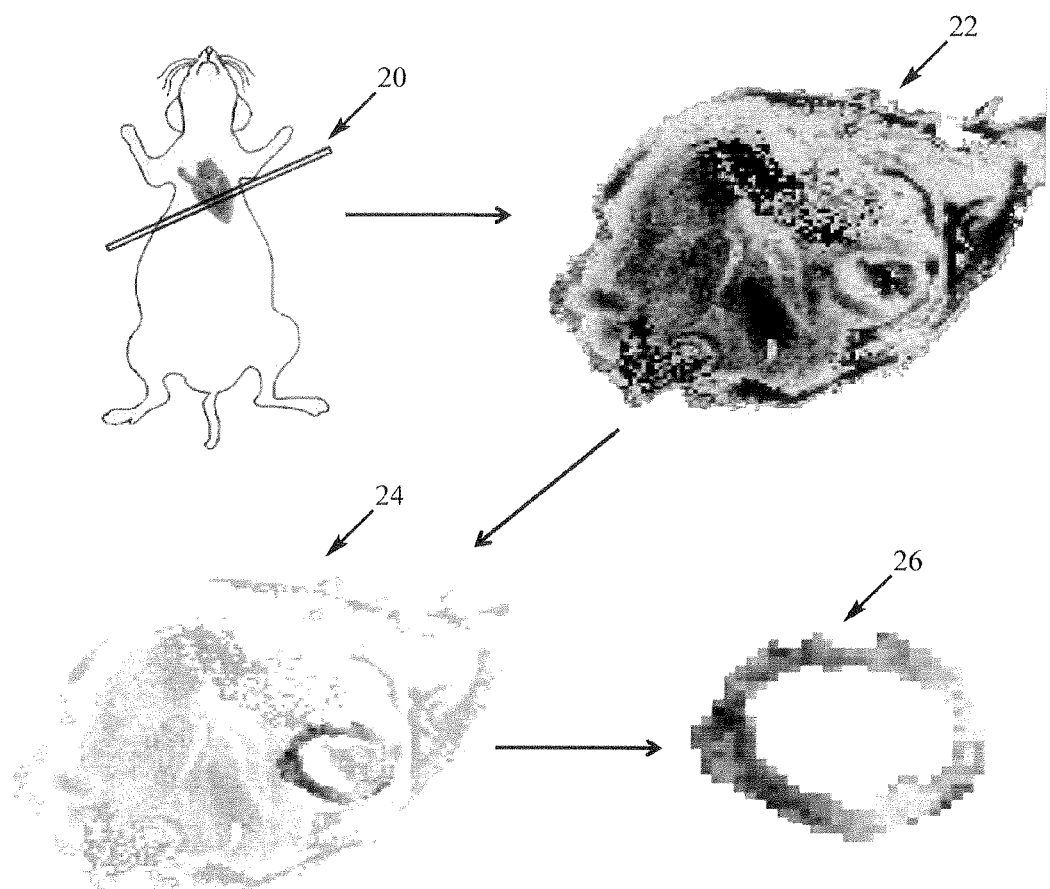
FIG. 2 shows an automated myocardial isolation flow chart. Representation of the short axis cardiac slice orientation (top left) used to acquire a short axis $T_1$-map of a MI mouse post-$MnCl_2$ infusion (top right). Input of this $T_1$ map with an associated $T_1$-weighted image, an unbiased isolation program was used to isolate the myocardial tissue from image (bottom left and right).

In certain aspects, it is desirable to obtain $T_1$ maps of specific anatomical regions of the organ and compare them to other regions in the organ. This ultimately can provide better insight as to the performance of one region of the organ compared to other regions. FIG. 2 provides an example of this aspect. Referring to FIG. 2, a cross-section of the heart is imaged (20) to produce a $T_1$-map 22 before and after administration of the manganese ions. From the $T_1$ map 22, a computer readable medium can be used to separate the myocardial tissue from the $T_1$-map 22 to generate myocardial tissue images 24 and 26. A detailed description of the computer readable medium useful herein is provided in the Examples. Although the methods described herein are useful in imaging the heart and measuring changes in efflux and influx $Mn^{2+}$ rates, the methods can be applied to other organs where it is desirable to measure changes in efflux and influx $Mn^{2+}$ rates and investigate calcium ion activity. For example, the brain, liver, kidney, pancreas, bladder, and spine, can be investigated using the methods described herein.

Figure 3:
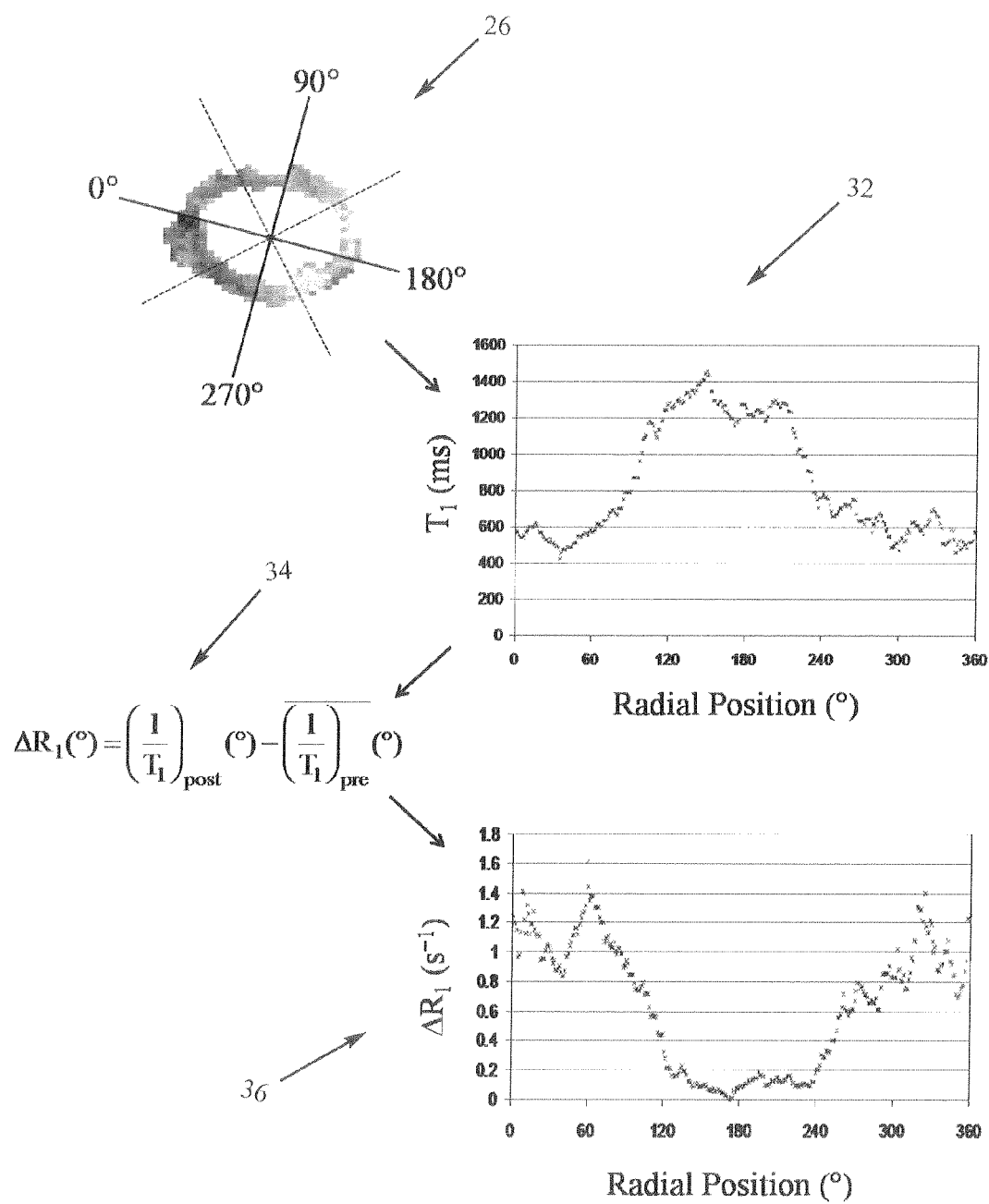
FIG. 3 shows a myocardium segmentation flow chart. The orientation definition (defined in the top image) is used to create a position dependent $T_1$ profile (top graph). Data from both pre- and post-$MnCl_2$ infusion $T_1$ maps are input into the shown equation, with a resultant output for the radial $\Delta R_1$, at a given time, shown (bottom graph).

Referring to FIG. 3, from the cross-section image of myocardial tissue 26, $T_1$ mapping of specific regions of the tissue cross-section before and after administration of the manganese ions can be performed. For example, $T_1$ values at specific radial positions can be determined (see 32 in FIG. 3). As discussed above, $\Delta R_1$ values can be calculated at specific radial positions in the tissue cross-section 26 using equation 34 in FIG. 3. The $\Delta R_1$ values can subsequently be plotted in a graph as depicted in 36 in FIG. 3. By plotting the $\Delta R_1$ values at different radial positions of the cross-section 26, it is possible to identify specific regions of the tissue cross-section that are experiencing changes in manganese ion efflux. Additionally, the $\Delta R_1$ values obtained from the MRI images can be correlated to appropriate manganese ions concentration from a standard manganese concentration dependent curve. The relevance of this is addressed in detail below.

The source of manganese ions can be administered to the subject orally, intravenously, subcutaneously, intramuscularly, intraperitoneal or any combination thereof. The source of manganese ions can be any compound or composition having manganese that produces manganese ions ($Mn^{2+}$). For example, when the manganese containing compound is administered to a subject, the manganese containing compound can produce manganese ions in vivo. Examples of manganese containing compounds include, but are not limited to, manganese chloride ($MnCl_2$), manganese dipyridoxyl diphosphate (MnDPDP), EVP 1001 (manganese gluconate/calcium gluconate 1:X manufactured by Eagle Vision and as described in detail in U.S. Pat. No. 5,980,863), TESLASCAN®, which is manafodipir trisodium, or any contrast agents which can release free manganese ions ($Mn^{2+}$). Manganese containing compounds may be used as contrast agents for imaging, such as imaging with an MRI (magnetic resonance imaging), because of the unique property of the constituent manganese ions to act as an intracellular contrast agent. Generally, contrast agents are a group of contrast media that are used to improve visibility of internal cellular structure and to improve visibility of internal body structures such as tissues within a subject. In one aspect, the manganese containing compound is manganese chloride or manganese dipyridoxyl diphosphate, which can dissociate in vivo into manganese ions and chloride or manganese ions and dipyridoxyl diphosphate, respectively. As stated herein, manganese ions can be taken up by the cell, and due to manganese ion's properties, act in manner similar to intracellular calcium ions while also acting as a suitable contrast agent. In one aspect, $Mn^{2+}$ uptake can occur in heart tissue and is mediated by voltage gated calcium channels such as, for example, the sodium-calcium exchanger.

The source of manganese ions can be formulated with a variety of pharmaceutically-acceptable carriers known to those skilled in the art. Examples of standard carriers for administration to humans include solutions such as sterile water, saline, and buffered solutions at physiological pH. In one aspect, the manganese containing compound can be administered to a subject via injection (e.g., intravenously, subcutaneously, intraperitoneal, and intramuscularly). Preparations for administration via injection include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. In certain aspects, a standard protocol, for example, the American College of Radiology's "Practice Guideline for the Use of Intravascular Contrast Media" (Revised 2007, Res. 39, Effective Oct. 1, 2007) may be followed for the administration of the contrast agents described herein.

It will be appreciated that the actual preferred amounts of the source of manganese ions administered to the subject can vary according to the particular compositions formulated, the mode of application, and the particular sites and mammal being treated. In order to quantify the manganese ion efflux and influx rates using the methods described herein, the initial concentration of the source of manganese ions administered to the subject needs to be known. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999)).

Once administered to the subject, the source of manganese ions begins to dissociate into manganese ions ($Mn^{2+}$), which are taken up by cells (e.g., myocardiate cells and cardiate cells). Numerous protein transporters aid in the cellular uptake of manganese ions. For example, the sodium and calcium exchanger and various other protein pumps, transporters, and exchangers facilitate the uptake of manganese ions. The cell generally requires some time to take up the manganese ions. The organ (or segment thereof) can be imaged multiple times after administration of the source of manganese ions. In one aspect, the organ is imaged from 1 to 6 times over a period of 30 minutes to 9 hours after step (b). The patient does not need to remain in the MRI machine if multiple images are to be taken over a prolonged period of time.

Figure 4:
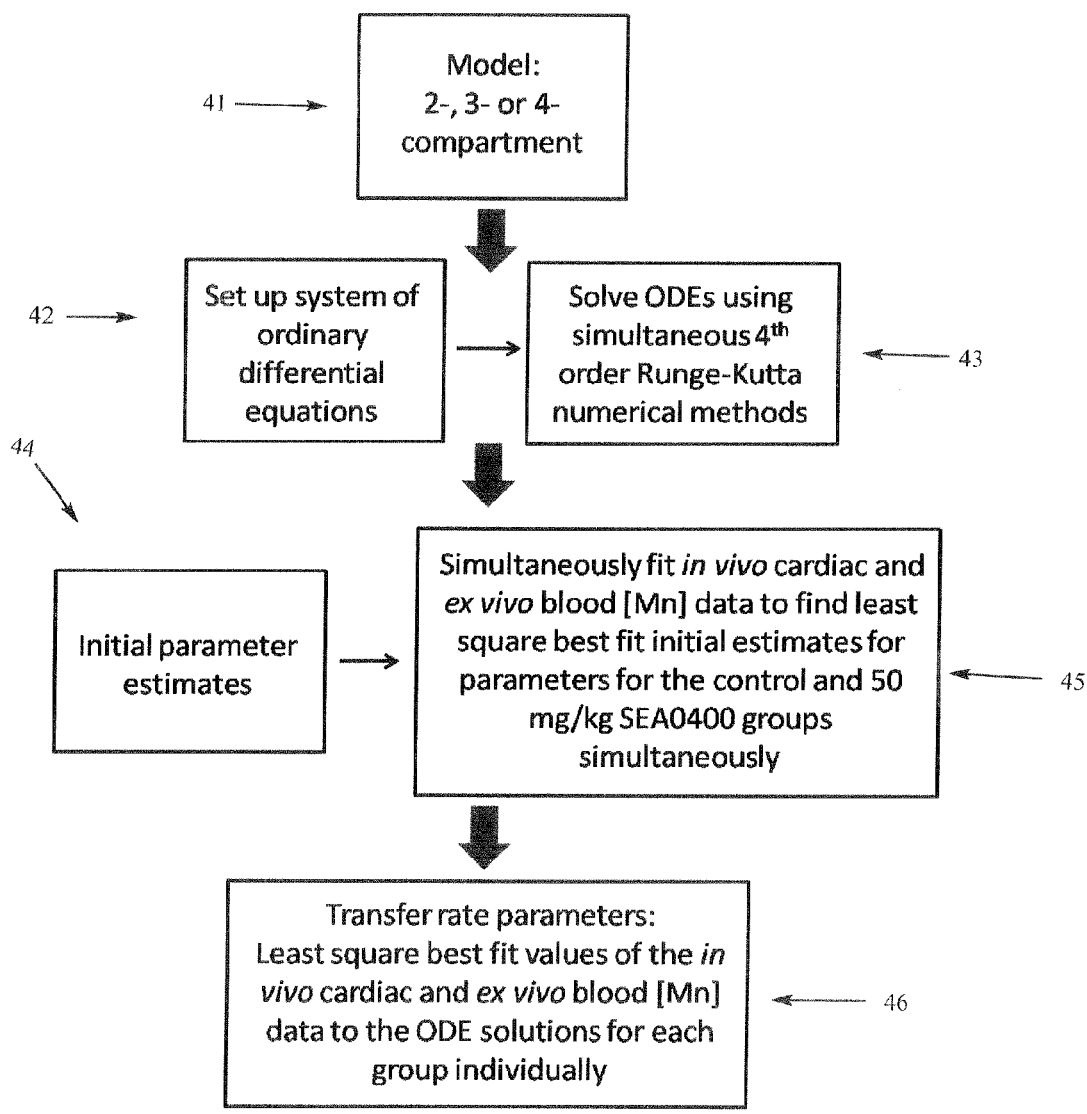
FIG. 4 shows a flow chart of the procedures involved with estimating the transfer rate and pharmaceutical parameters using pharmacokinetic modeling.
Figure 6:
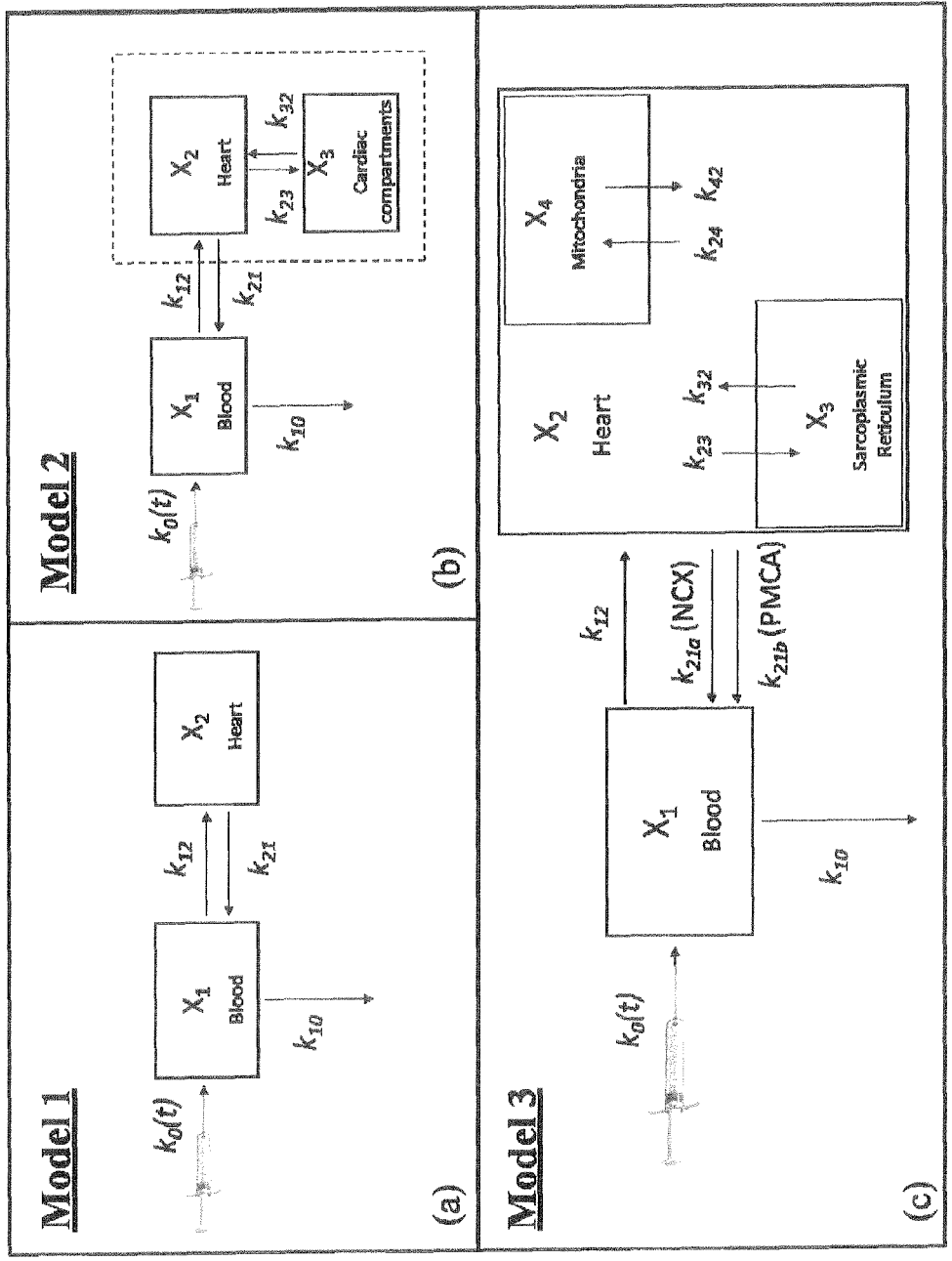
FIG. 6 shows schematic representations of pharmacokinetic Models 1 (a), 2 (b) and 3 (c).

After imaging the organ of interest, manganese ion concentrations can be compared to a standard multi-compartment (i.e., two or more compartments) pharmacokinetic model of a healthy organ. A detailed discussion regarding the generation of pharmacokinetic models useful herein is provided in the Examples. FIG. 4 depicts a flow chart for estimating transfer rates and pharmaceutical parameters based on pharmacokinetic models useful herein. The first step as shown in FIG. 4 is to select the appropriate model with compartments (41 in FIG. 4). Examples of models useful for evaluating manganese ion efflux and influx in the heart can be found in FIG. 6. Referring to model 1 in FIG. 6, this is a two compartment model (blood and heart). Model 2 has three compartments (blood, heart, and cardiac compartments), and model 3 has four compartments (blood, heart, mitochondria, and sarcoplasmic reticulum). For each compartment, there is a transfer rate for manganese ion to and from the compartments. For example, in model 1, $k_{12}$ is the transfer rate of manganese ion from the blood compartment to the heart compartment (i.e., the influx rate). Conversely, $k_{21}$ is the transfer rate of manganese ion from the heart compartment to the blood compartment (i.e., the efflux rate).

A system of ordinary differential equations is set up for each model (42 in FIG. 4). Solutions to the ODEs can be acquired by mathematical techniques such as, for example, $4^{th}$ Order Runge-Kutta numerical methods (43 in FIG. 4). Concurrently, in vivo imaging data and ex vivo blood [Mn] are fitted using mathematical techniques in order to find the least square best fit initial estimates for pharmaceutical parameters (45 in FIG. 4). Finally, transfer rate parameters are determined by the least square best fit values of the in vivo imaging data and ex vivo blood [Mn] data to the ODE solutions for each group individually (46 in FIG. 4).

Figure 10:
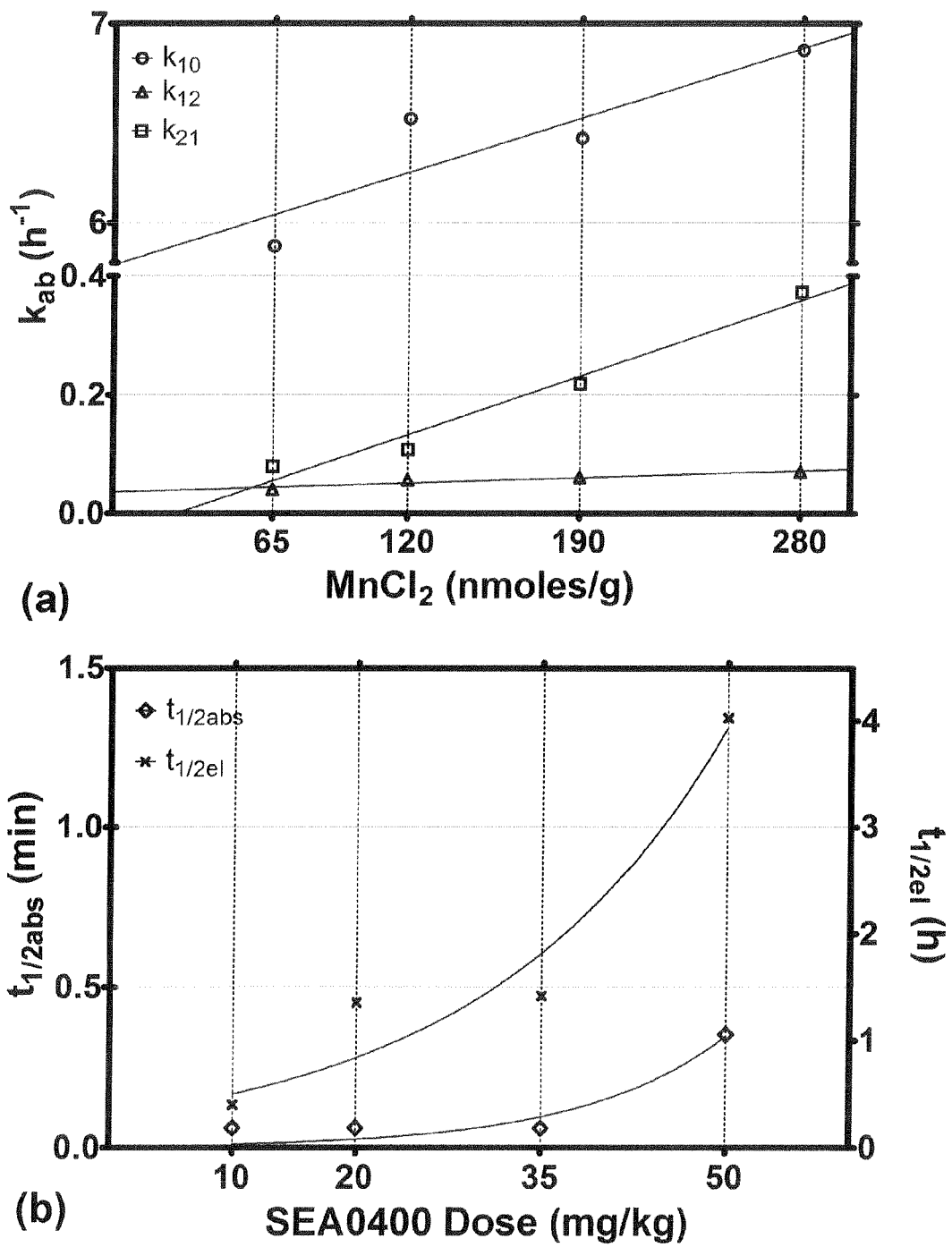
FIG. 10 shows dose dependent trends for the transfer rate parameters (a) and pharmaceutical absorption and efflux half-lives (b) predicted by the best model (Model 1 for all groups except the 50 mg/kg SEA0400 group, which is improved with Model 2). Also shown are linear least square and exponential best fits for the transfer rate parameters (a) and half-lives (b) respectively.

Ultimately, the transfer rate parameters are used to produce standard curves that can be compared to imaging data from a subject that is experiencing changes in manganese ion efflux or influx when administered the source of manganese ions (i.e., the contrast agent). An example of this application is provided. FIG. 10, shows (a) dose dependent trends for the transfer rate parameters and (b) pharmaceutical absorption and efflux half-lives predicted by model 1 in FIG. 6 (blood and heart) for all groups except the 50 mg/kg SEA0400 group (see Examples). From the efflux transfer rate parameter ($k_{21}$) in FIG. 10a, efflux half-lives can be plotted at different concentrations of manganese ion source administered to a healthy subject. This plot is found in FIG. 11c, where the exponential half-life is plotted vs. different concentrations of $MnCl_2$ that is administered to a healthy subject (e.g., a healthy mouse in this example).

The plot in FIG. 11c is an example of a standard pharmacokinetic model useful herein, which takes into account manganese ion efflux rates from the heart compartment to the blood compartment at different manganese ion concentrations administered to the subject. With respect to the subject, the organ of interest or segment thereof is imaged to obtain a pre-$T_1$ map. The subject is administered a known concentration of contrast agent (i.e., source of manganese ions). Next, the organ or segment thereof is imaged at specified time intervals to obtain post-$T_1$ maps. FIGS. 11a and 11b are in vivo imaging data taken from a subject. FIG. 11a is a graph showing radial $\Delta R_1$ at a given time using a segmenting system 80 described herein for a subject experiencing myocardial infarction after administration of the contrast agent. Referring to FIG. 11a, radial positions a-c and c-d are peri-infarcted (PI) zones, while radial position b-c is necrosed tissue. FIG. 11b shows the temporal efflux rates at a specific radial position from FIG. 11a. At any given concentration of contrast agent, temporal $\Delta R_1$ values can be converted to exponential half-life values and compared to the plot in FIG. 11c for a healthy subject. For example, if the subject was administered 120 nmoles/g $MnCl_2$, the resulting exponential half-life can be derived from the temporal $\Delta R_1$ values at a specific time and location (FIGS. 11a and 11b) in the organ to assess manganese ion efflux. Thus, in one aspect, if the exponential half-life falls below the curve in FIG. 11c at 120 nmoles/g $MnCl_2$, there is an increase in manganese ion efflux from the heart to the blood with the proper concentration of contrast agent administered to the subject. Furthermore, when comparing the in vivo imaging data to the standard pharmacokinetic model in FIG. 11c, it is possible to quantify $Mn^{+2}$ ion efflux rates from specific regions and times of the infarcted myocardium. This is one of the many advantages of the methods and systems described herein that is not possible with current techniques.

The fact that FIG. 11c factors out concentration of contrast agent in the efflux rates provides a powerful tool in monitoring manganese efflux rates. Based on the models of the heart, there is an apparent increase in the $Mn^{2+}$ efflux rate from ischemic tissue, commensurate with increased $Mn^{2+}$ content in viable cells within these regions. This effect has been widely observed for ex vivo $Ca^{2+}$ transport, but has thus far proved elusive for in vivo MEMRI studies. The predictions made by the methods described herein allow for a more thorough understanding of the relationship between $Mn^{2+}$ and relative $Ca^{2+}$ handling in the heart. This approach therefore has the potential to be applied as a diagnostic tool in the early detection of abnormal $Ca^{2+}$ handling in the myocardium, and for monitoring disease progression.

Additionally, the methods described herein can further assist the physician in the treatment of certain diseases associated with changes in $Mn^{+2}$ and relative $Ca^{+2}$ efflux or influx rates. For example, manganese ion efflux can occur via different mechanisms. An example of this can be found in model 3 of FIG. 6, which includes NCX and PMCA efflux mechanisms. By understanding which mechanism is responsible for $Mn^{+2}$ efflux, it is possible select the appropriate treatment to prevent further efflux and prevent further damage to the organ. For example, therapeutic agents may be administered in a dose dependent manner based on the efflux rate of $Mn^{2+}$. Therapeutic agents may include, for example, any therapeutic agent that affects $Mn^{2+}$ and $Ca^{2+}$ flux dynamics or fluctuations such as angiotensin converting enzyme (ACE) inhibitors, $Ca^{2+}$ channel blockers, NCX inhibitors, and any $Ca^{2+}$ flux modulating compounds/therapeutics. In certain aspects, this tailored treatment regimen may be further monitored by the methods described herein, by routine clinical laboratory tests, and by other techniques known in the art. Based on these results, a subject's treatment regimen (i.e. dosing schedule and amounts) may be further tailored to meet that individual's needs or discontinued.

Figure 5:
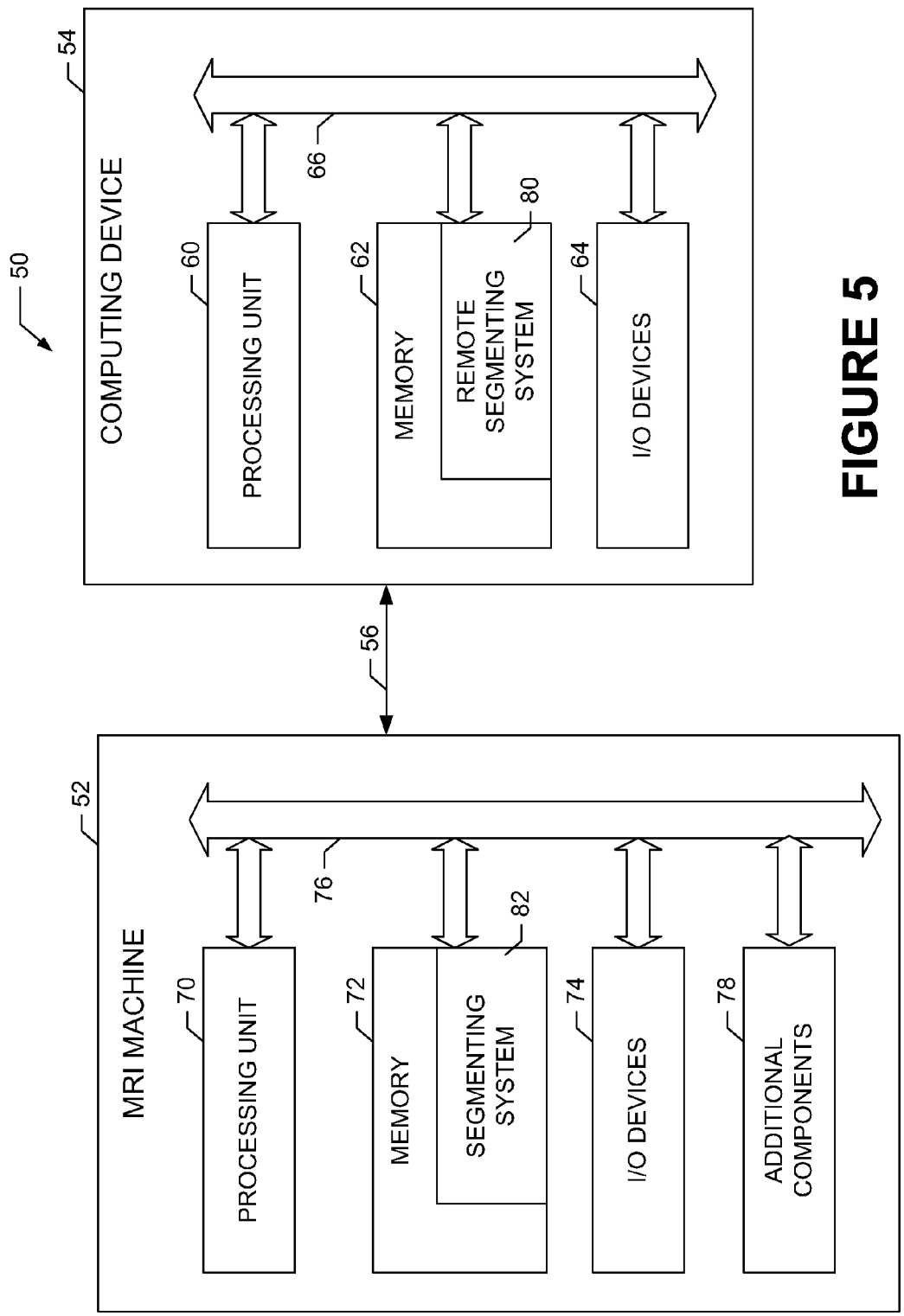
FIG. 5 depicts a block diagram of an example of a suitable computing system environment on which the invention may be implemented.

With reference to FIG. 5, an exemplary system 50 for implementing the data acquisition (i.e., imaging) and data analysis (e.g., measuring manganese ion efflux concentration) includes a conventional MRI machine 52 configured for MEMRI imaging coupled to a general-purpose computing device in the form of a computer 54. The MRI machine 52 can be operatively coupled to the computer 54 via a suitable interface 56, such as a cable or via one or more networks, including but not limited to: the Internet, a local area network (LAN), a wide area network (WAN), via a telephone line using a modem (POTS), Bluetooth, WiFi, cellular, optical, satellite, RF, Ethernet, magnetic induction, coax, RS-485, or other like networks. In such an embodiment, data obtained from scans by the MRI device 52 can be transmitted to the computer 54 for further manipulation.

Components of computer 54 may include, but are not limited to, a processing unit 60, a system memory 62, i/o devices 64, and a system bus 66 that couples various system components including the system memory to the processing unit. All of the components of the computer 54 are conventional and well known to those skilled in the art.

For example, the processing unit 60 is a hardware device for executing software that can be stored in memory 62. The processing unit 60 can be virtually any custom made or commercially available processor, a central processing unit (CPU), data signal processor (DSP) or an auxiliary processor among several processors associated with a server, and a semiconductor based microprocessor (in the form of a microchip) or a macroprocessor. Examples of suitable commercially available microprocessors are as follows: an 80x86 or Pentium series microprocessor from Intel Corporation, U.S.A., a PowerPC microprocessor from IBM, U.S.A., a Sparc microprocessor from Sun Microsystems, Inc, a PA-RISC series microprocessor from Hewlett-Packard Company, U.S.A., or a 68xxx series microprocessor from Motorola Corporation, U.S.A.

Memory 62 can include any one or combination of volatile memory elements (e.g., random access memory (RAM, such as dynamic random access memory (DRAM), static random access memory (SRAM), etc.)) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 62 may incorporate electronic, magnetic, optical, and/or other types of storage media. Note that the memory 62 can have a distributed architecture, where various components are situated remote from one another, but can be accessed by the processing unit 60.

Input/output devices 64 can include one or more of the following: a keyboard, a microphone, a pointing device, such as a mouse, trackball or touch pad, a joystick, game pad, satellite dish, scanner, monitor, display device, speaker, printer, or the like.

The system bus 66 can be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Additionally or alternatively, the methods of the present invention can be implemented in a conventional MRI machine having computing components similar to the computer 54, including a processing unit 70, a system memory 72, i/o devices 74, and a system bus 76 that couples various system components including the system memory to the processing unit 60, in addition to the conventional MRI components 78 (such as a coil, magnets, etc.). MRI machines are well known in the art, and thus, the internal components will not be discussed in detail.

The methods of the present invention can be embodied in a segmenting system 82 on the MRI machine 52 or in a remote segmenting system 80 on a computing device 54 coupled to the MRI machine. The segmenting system 82 and remote segmenting system 82 of the invention may be embodied in hardware (such as in the processing unit 70 or memory 72 of the MRI machine 52 or in the processing unit 60 or memory 62 of the computer 54 or computing device operatively connected to an MRI machine) and/or in software (including firmware, resident software, micro-code, etc.). If implemented in hardware, a system of the present invention be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The segmentation systems 80 and 82 may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. Computer readable media can be any available media that can be accessed by a computer or computing device and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computer. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means (i.e., modules such as baseline module, concentration module, comparison module, calculating module, and map module) for carrying out the functions of the invention in the example embodiments and as recited in the claims.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric.

I. METHODS AND MATERIALS

In vivo MEMRI $T_1$-mapping efflux studies were conducted in adult male C57Bl/6 mice (6-14 weeks old, 23.9±2.3 g). All experiments followed the guidelines of the Institutional Animal Care and Use Committee at the Medical College of Georgia, Augusta, Ga., USA, as previously described.

$MnCl_2$ infusions (prepared from a 60 mM stock solution) were administered intravenously via the tail vein, at a constant rate ($k_0$) of 0.6 ml h$^{-1}$ (=3.6×10$^4$ nmoles h$^{-1}$) with the aid of a syringe pump (KD Scientific Inc., Holliston, Mass., USA). The total infusion time, T (h), was therefore dependent on the infusion dose and mouse body weight (BW) (Eq. [1]).

$$k_0(t) = \begin{cases} k_0 & 0 \le t \le T \\ 0 & t > T \end{cases} \quad (1)$$

The mice were randomized into three groups for efflux studies:
1) $MnCl_2$ dose dependent (65±0.2, 119±2, 190±3 (Control) and 283±6 nmoles/g body weight $MnCl_2$, n=40 mice)
2) SEA0400 dose dependent (190±1 nmoles/g BW $MnCl_2$ infusion, followed 1 hour later with an i.p. injection of 10±0.2, 20±0.2, 34±0.8 and 50±0.2 mg/kg SEA0400, n=30)
3) Myocardial infarction (MI, 190±0.1 nmoles/g BW $MnCl_2$, n=9)

Table 1 shows the total study sizes (number of mice and total number of $T_1$-maps post-$MnCl_2$ infusion), $MnCl_2$ infusion doses (nmoles/g BW), and pharmaceutical doses for each group.

Washout curves were obtained for each group, showing changes in left ventricular free wall (LV Wall) relaxation rate, $\Delta R_1 = 1/T_1(\text{post-}) - 1/T_1(\text{pre-MnCl}_2)$ infusion. Elemental analysis data, using inductively coupled plasma-mass spectrometry (ICP-MS) analysis (CANTEST Ltd., North Vancouver, BC, Canada), were acquired from select heart (n=29) and blood (n=26) samples to obtain the absolute sample Mn content. A correlational analysis was performed between the ex vivo data to in vivo $\Delta R_1$ data, to obtain a relationship between the increase in Mn content and $\Delta R_1$.

Manganese-Enhanced Magnetic Resonance Imaging

MEMRI data were acquired on a 7.0-T 20-cm horizontal bore Bruker BioSpec MRI spectrometer (Bruker Instruments, Billerica, Mass.) equipped with a micro-imaging gradient insert (950 mT/m). A standard Bruker volume coil (35 mm inner diameter) was used to transmit and receive at $^1$H frequency (300 MHz). The electrocardiographic (ECG) and respiratory signals were monitored by a physiological monitoring system (SA Instruments, Inc., Stony Brook, N.Y.). The R wave of the ECG signal was used to gate all images. Short-axis images were acquired midway through the LV and perpendicular to the long axis of the heart. For the MI group, the short-axis slice contained the area with the thinnest portion of the LV wall (typically located within 1 mm of the LV center).

All $T_1$ maps were acquired with an ECG-gated, flow-compensated Look-Locker MRI pulse sequence using these parameters: matrix=128×128; TE/TR=2.5 ms/10 s; slice thickness=1.0 mm; FOV=3.0×3.0 cm; NA=2; inversion time=9 ms; average echo interval=138 ms (determined in each case using the average observed R-R wave interval before acquisition); number of echo images=50; average flip angle=11±1°. The initial inversion pulse per repetition was gated by separating the constant echo interval from the subsequent echo pulses, which minimized the R-R interval fluctuations. From the duration of the $T_1$ map acquisition (~43 min), individual data points were defined to have been acquired at the center of k-space, approximately 21.5 minutes after initiation of the imaging sequence.

Pharmacokinetic Models

The $MnCl_2$ pharmacokinetic properties, with and without use of SEA0400, were modeled using three models: Model 1 (FIG. 6a) was a two-compartment model, representing the blood and heart; Model 2 (FIG. 6b) was a three-compartment model, consisting of blood, cytosolic free $Mn^{2+}$ and cytosolic compartmentalized $Mn^{2+}$; Model 3 (FIG. 6c) contained four compartments for the blood, cytosolic free $Mn^{2+}$, sarcoplasmic reticulum and mitochondria compartments.

For each of the models, $MnCl_2$ was infused into the blood compartment at a rate of $k_0(t)$, as given in Eq. [1], with the infusion duration, T, dependent on the mouse BW. First order rate parameters, $k_{ab}$ [h$^{-1}$] (FIG. 6), were used to describe the rate of transfer from compartment a to b, where $k_{10}$ is defined as the rate parameter for $Mn^{2+}$ efflux from the blood to organs other than the heart (e.g. liver, kidney and other major organs).

For the SEA0400 group, the NCX inhibitor was administered one hour post-$MnCl_2$ infusion with the expected effect of reducing the cardiac efflux transfer rates, dependent on the drug's absorption and elimination rates. In order to model the drug pharmacokinetics of SEA0400, and therefore the $Mn^{2+}$ transport mechanisms, an equation for the drug plasma concentration ($C_p$) was used (Eq. [2]), commonly applied to pharmaceutical modeling:

$$C_p(t) = \frac{FD}{V_d} \frac{k_{abs}}{(k_{abs} - k_{el})} (e^{-k_{el} \cdot t} - e^{-k_{abs} \cdot t}) \quad (2)$$

In Eq. [2] F is the fraction of drug absorbed, $V_p$ is the apparent volume of distribution of the drug and D is the drug dose administered. The rate parameters, $k_{el}$ and $k_{abs}$ represent the drug elimination and absorption rates respectively.

The form for the $Mn^{2+}$ transfer rate parameter $k_{21}$ was given by Eq. [3], under the assumption that $k_{21}$ decreases linearly with increasing SEA0400 plasma concentration, $C_p$, as in Eq. [2]:

$$k_{21}(t \geq 1) = k_{21,initial}\left(1 - \frac{k_{abs}}{(k_{abs} - k_{el})}(e^{-k_{el} \cdot (t-1)} - e^{-k_{abs} \cdot (t-1)})\right) \quad (3)$$

Parameter $k_{21,initial}$ is defined as the pre-pharmaceutical administration transfer parameter, $k_{21}(t<1\ h)$. Due the relatively fast blood pool clearance, on order to 12 minutes, and the fact that SEA0400 was administered one hours post-MnCl$_2$ infusion, $k_{12}$ is not expected to change appreciably following SEA0400 administration. All the transfer rate and pharmaceutical parameters were therefore time-independent with the exception of $k_0$ and $k_{21}$ following SEA0400 administration.

The pharmaceutical absorption and elimination half-live ($t_{1/2abs}$ and $t_{1/2el}$ respectively) are given in Eq. [4] and Eq. [5].

$$t_{1/2abs} = \frac{\ln(2)}{k_{abs}} \quad (4)$$

$$t_{1/2el} = \frac{\ln(2)}{k_{el}} \quad (5)$$

For all of the models, a system of ordinary differential equations (ODEs) was obtained, dependent on the number of compartments and transfer rate parameters. The individual models and ODEs are described in more detail in the following subsections, and are summarized in Table 2.

Solutions to the ODEs were acquired using simultaneous $4^{th}$ Order Runge-Kutta numerical methods in Matlab (Nantick, Mass.). Temporal in vivo cardiac Mn$^{2+}$ content data and ex vivo blood Mn$^{2+}$ content data were fit simultaneously to acquire least square fits for the first order rate parameters, $k_{ab}$. Least square fits of the pharmaceutical parameters, $k_{abs}$ and $k_{el}$ were also obtained using the SEA0400 groups, assuming that $k_{ab}$ was unchanged from the control 190 nmoles/g group. Parameter $k_{21,initial}$ (Eq. [3]) was defined as the best fit $k_{21}$ parameter using the control 190 nmoles/g BW group. The only constraint made by the least square fitting technique was that the transfer rate parameters and pharmaceutical parameters were $\geq 0$.

Least square curve fitting techniques are inherently sensitive to the initial estimates of $k_{ab}$. For a given initial estimate of $k_{ab}$ the fit may converge on solutions at local minima, which may not be the global minimum. In order to minimize potential errors caused by this effect, all the models employed a global search over a wide range in parameter space to find the initial estimates of $k_{ab}$ corresponding to lowest fit residuals. To use the most realistic initial estimates for the fitting function, simultaneous solutions were obtained for the control 190 nmoles/g heart and 50 mg/kg SEA0400 heart efflux data, as well as the corresponding blood efflux data. All models assume that the two efflux groups share the same transfer rate parameters, with only $k_{21}(t)$, characterized by $k_{abs}$ and $k_{el}$, being affected by administration of SEA0400.

Model 1—Two-Compartment Model

Model 1 contains components representing the blood and myocardium (FIG. 6a) with the absolute Mn content for each given by $X_1(t)$ and $X_2(t)$ [nmoles] respectively.

A system of ordinary differential equations (ODEs) was setup with dependent variables $X_1$ and $X_2$, and independent variable $t$ [h], as shown in Eq. [6].

$$\frac{dX_1}{dt} = k_0(t) - (k_{10} + k_{12})X_1(t) + k_{21}X_2(t) \quad (6)$$

$$\frac{dX_2}{dt} = k_{12}X_1(t) - k_{21}X_2(t)$$

For the SEA0400 groups, a similar set of simultaneous ODEs was used, with $k_{21}$ modeled as a function of time (Eq. [3]). This function was also applied to the SEA0400 groups for the following models.

Model 2—Three-Compartment Model

In order to address the kinetics of Mn$^{2+}$ compartmentalization within the myocardium, a third compartment was added (FIG. 6b). Free Mn$^{2+}$ was assumed to reside in compartment 2, but a third compartment representing the compartments within the myocyte (e.g. mitochondria and SR) was assumed. Rate parameters $k_{23}$ and $k_{32}$ define the uptake and release rates respectively for the third compartment as the sum of individual compartments.

A system of ordinary differential equations (ODEs) was setup for this model as shown in Eq. [7].

$$\frac{dX_1}{dt} = k_0(t) - (k_{10} + k_{12})X_1(t) + k_{21}X_2(t) \quad (7)$$

$$\frac{dX_2}{dt} = k_{12}X_1(t) - (k_{21} + k_{23})X_2(t) + k_{32}X_3(t)$$

$$\frac{dX_3}{dt} = k_{23}X_2(t) - k_{32}X_3(t)$$

Least square best fit values for the rate parameters ($k_{ab}$) were acquired following simultaneous least square fitting for both the blood ($X_1$) and heart ($X_2 + X_3$) compartments.

Model 3—Four-Compartment Model

The four-compartment model was designed for the most physiological and anatomical specificity. The model contains two cytosolic compartments, representing the SR (compartment 3) and mitochondria (compartment 4), in addition to the free cytosolic Mn$^{2+}$ (compartment 2). Additionally, efflux from the myocardium was modeled using two efflux rates, $k_{21a}$ and $k_{21b}$, representing the NCX and PMCA efflux mechanisms respectively. The ODEs for this model are shown in Eq. [8].

$$\frac{dX_1}{dt} = k_0(t) - (k_{10} + k_{12})X_1(t) + (k_{21a} + k_{21b})X_2(t) \quad (8)$$

$$\frac{dX_2}{dt} = k_{12}X_1(t) - (k_{21a} + k_{21b} + k_{23} + k_{24})X_2(t) + k_{32}X_3(t) + k_{42}X_4(t)$$

$$\frac{dX_3}{dt} = k_{23}X_2(t) - k_{32}X_3(t)$$

$$\frac{dX_4}{dt} = k_{24}X_2(t) - k_{42}X_4(t)$$

It is possible that differences exist in the longitudinal relaxivity, $r_1$, between cytosolic Mn$^{2+}$ in compartment 2 and the compartmentalized Mn$^{2+}$ in compartments 3 and 4, possibly due to the binding of Mn$^{2+}$ to larger molecules within the compartments or to potential chelation of the free Mn$^{2+}$ ions. To model this phenomenon, an additional function was added.

Equation [9] demonstrates the relationship between the changes in relaxation rates between the compartments.

$$\Delta R_{1,T} = \Delta R_{1,cytosolic} + \Delta R_{1,comp}$$

$$\Delta R_{1,T} = r_{1,T} \cdot X_T; \Delta R_{1,cytosolic} = a \cdot X_2; \Delta R_{1,comp} = b \cdot (X_3 + X_4)$$

$$X_T = 1/r_{1,T}(a \cdot X_{cytosolic} + b \cdot X_{comp}) \quad (9)$$

From Eq. [9], $r_{1,T}$, is defined as the ratio between in the in vivo cardiac $\Delta R_1$ values and the increase in Mn content. $\Delta R_{1,T}$, $\Delta R_{1,cytosolic}$ and $\Delta R_{1,comp}$ represent the change in relaxation rates for the total heart (combined compartments 2, 3 and 4), cytosolic Mn (compartment 2) and compartmentalized Mn (compartments 3 and 4), respectively, with weighting constants a and b proportional to the relaxivities of compartment 2 and 3, respectively. The total cytosolic and compartmentalized Mn content was therefore $a/r_{1,T} \cdot X_{cytosolic}$ and $b/r_{1,T} \cdot X_{comp}$, respectively, using solutions to Eq. [8], $X_{cytosolic}$ (=$X_2$) and $X_{comp}$ (=$X_3 + X_4$).

To reduce the number of variables in Model 4 for better model behavior while maintaining realistic physiological constraints, the following relationships were used for the rate parameters (Eq. [10] and Eq. [11]), all derived from literature regarding $Ca^{2+}$ transfer rates:

$$k_{21a} = 0.8 \cdot k_{21total}; k_{21b} = 0.2 \cdot k_{21total} \quad (10)$$

$$k_{23} = 0.9 \cdot k_{2comp}; k_{24} = 0.1 \cdot k_{2comp} \quad (11)$$

$k_{21total}$ and $k_{2comp}$ are the total transfer rates from compartment 2 to the blood, and from compartment 2 to compartments 3 and 4, respectively. These two parameters were estimated via the modeling technique. SEA0400 was assumed only to reduce the rate of $Mn^{2+}$ efflux via the NCX ($k_{21a}$), with $k_{21a}$ therefore being modeled as a function of time using Eq. [3].

Statistics

For all the models, the residuals and coefficient of determination, $R^2$, were calculated. The models were then compared to each other using an F test, both for individual efflux study groups as well as an overall model comparison for all of the efflux groups combined. These tests were used to ascertain whether potential decreases in sum-of-squares for the more complicated models outweighed the loss of degrees of freedom following increased numbers of fit parameters. The level of significance was set at 0.05. For comparison, a first-order exponential fit was also made for the efflux data, corresponding to a simple one-compartment model with no physiological detail.

Segmenting System

In one example embodiment, the segmenting systems 80 or 82 utilize scripts written in Matlab (Natwick, Mass.). Since segmenting systems 80 and 82 operate in a similar manner, hereafter, when segmenting system 80 is referred to, it implies segmenting system 80 or segmenting system 82 for the sake of brevity. The segmenting system 80 segments the myocardium into a $T_1$-map having angular segments or "sectors." The segmenting system 80 operates in three modes. In "Process" mode, myocardium data for an individual animal is processed. The segmenting system output for this mode includes graphical plots, showing mean $T_1$, $R_1$, and myocardial thickness values as scaled by color (see FIG. 12). These are plotted on an "idealized" short-axis view of the left ventricle myocardium, using the right ventricle as a spatial reference. The segmenting system 80 also creates a text file containing the following parameters for each angular sector: sector number, initial and final angular extension of the sector, number of pixels in the sector, mean and standard deviation of $T_1$ in the sector, mean thickness of the myocardium, and mean distance to inner surface of the left ventricle wall. In the "Plot" mode, datafiles created during the "Process" mode can be imported and re-plotted for graphical capture and inclusion in a manuscript or presentation. In the "Stats" mode, multiple files created during the "Process" mode can be imported for statistical analysis. All operations are handled through a graphical user interface (GUI).

Mode I: Process

This mode utilizes a $T_1$-weighted (T1W) image and a $T_1$ map for segmentation of the myocardium with minimal user input. After the image files are selected via graphical user interface (GUI), the user is asked whether or not the T1W image was acquired before or after administration of Mn contrast agent. Finally, the segmenting system 80 requests a minimum and maximum value of $T_1$ for consideration during the plotting process.

The purpose of the T1W image is to provide enhanced contrast between tissue and blood in the heart, allowing for easy segmentation of the myocardium. After the user inputs data and answers listed in the previous paragraph, the image intensities in the T1W image are binned into a histogram for separation of three image regions: air, tissue, and blood. Given an approximate blood threshold, the value is boosted to yield another estimate that is very conservative. The calculation of the blood threshold is automatically adjusted if the image is not acquired after administration of Mn contrast agent.

Final input from the user is requested. A graphical window showing the $T_1$-map is displayed on the screen. Using a mouse, the user chooses the approximate center of the heart chamber, chooses the approximate center of the right ventricle chamber, then clicks to agree with these choices. The actual center is found using pixels identified as a volume of blood from the approximate threshold, contiguous to the center chosen by the user. All angles are defined from the line extending between this center point and the user-chosen center point of the right ventricle, defined as 0°. At the same time, blood in the right ventricle is used to calculate an upper limit to the radial size of the left ventricle. Data located between the blood chamber (using the conservative threshold) and the radial limit of the myocardium as the raw myocardium, for further refinement.

Figure 12:
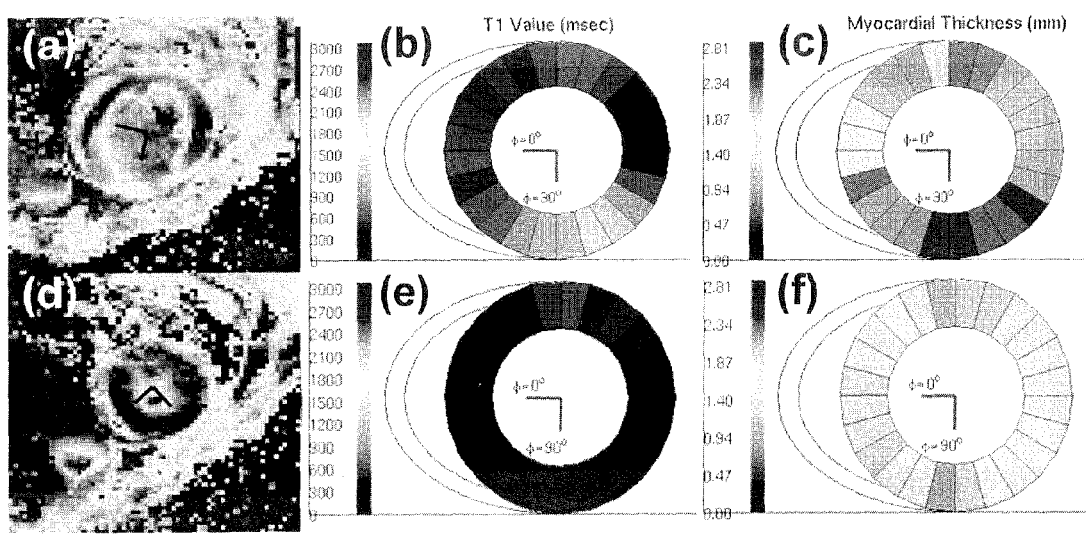
FIG. 12 shows the segmenting of myocardium post-$Mn^{2+}$ infusion with $T_1$ mapping: (a) $T_1$ map of a mouse with myocardial infarction; (b) the outline and division into sectors of the left ventricle, along with superimposed $T_1$ color division into sectors of the left ventricle, along with superimposed $T_1$ color maps of the slice from the respective measurements; (c) the outlines of the wall thickness map in diastole in millimeters; (d) $T_1$ map of a mouse with sham operation; (e) corresponding $T_1$ map segmentation for the mouse with sham operation; and (f) corresponding wall thickness map for the mouse with sham operation. After segmentation, the myocardium is segmented into angular sectors for calculation of mean $T_1$ value and thickness as well as sector variance. The figure shows a typical example of a myocardial infarction region, where the $T_1$ value remains long compared to normal tissue and where the myocardium undergoes thinning. In addition to eliminating the user-dependency of ROI designation, the segmentation process eliminates the ROI placement issues by orienting data according to left ventricle position. Furthermore, numerical output for each sector includes cardiac volume so that more rigorous analytical treatment can proceed.

In a $T_1$-map, the intensity of the myocardium should be darker than surrounding tissue and blood (FIG. 12). In the next stage, the program finds the approximate "trough" or minimum intensity as a function of angle of rotation from the 0° reference. Although this function may not be perfectly smooth, it forms the basis of an ellipse that traces the middle of the myocardium. After applying some low-pass filtering of the trough position as a function of angle (retaining the largest few Fourier components), the approximate center of the myocardium has been defined. Next, as a function of angle, the mean intensity of the myocardium is calculated. A similar smoothing process is applied to this function.

With a mean intensity value for the myocardium in the $T_1$-map (as a function of angle) and the mean position of the myocardium as a function of angle, the full myocardium is segmented as a function of angle, considering the following factors:

(1) An intensity threshold, which varies as a function of the mean myocardium intensity at that angular position. This is necessary to mirror the properties of the healthy and infarcted myocardium. The use of a simple standard deviation as a threshold leads to inclusion of extra tissue and blood around the infarct.

(2) An intensity threshold to exclude blood.

Finally, binary spatial filtering allows for the removal of stray individual pixels that appear connected on the edge of the myocardium due to noise.

Using the 0° reference line, sectors are defined with width 360o/N, where N is the number of sectors (nominally 24, but can be manipulated by the user). $T_1$ values for the pixels in the myocardium that fall within each sector are averaged, and the results plotted. A data file is generated with this information.

Mode II: Plot

The plotting in this mode is identical to the plotting in the previous mode. After input of the data files from previous "process" sessions, data is plotted to the screen.

Mode II: Stats

The stats mode takes data from the "process" mode and allows for processing of group statistics as a function of sector. Two types of stats are provided: "single group", and "multiple group." In both cases, data in each sector are normalized in the following manner, per animal. The sector at 270° is defined as the reference sector, showing no infarction. For each other sector, a value of $T1_{sector}/T1_{reference}$ is calculated (hereafter referred to as "$T_1$ norm"). Using these values, each sector in the group of mice yields a mean value and standard deviation of $T_1$ norm.

For the "single group" stats, data from all the mice are considered to belong to one group. For each sector, a t-score is calculated, using the $T_1$ norm from the reference and given sectors and using the sample standard error of the mean from both sectors. For "multiple group" stats, an F-test is performed per sector, considering the standard deviations in each sector in each group and the combined standard deviation for all groups. Results are plotted graphically.

Myocardial Infarction

For each $T_1$ map in the MI group, the segmenting system 80 described above was used to isolate the myocardium from the remaining tissue. The isolated myocardium was then segmented into 360×1° radial segments, where each sector contained approximately 4 voxels. Within each segment (with the center of the necrotic region shifted to 180°), the average $T_1$ values were determined, and the associated regional $\Delta R_1$ values calculated. Average $\Delta R_1$ values were calculated for the observed plateaus of the remote viable tissue (Region A) and the necrotic tissue (region B). Temporal average $\Delta R_1$ values for regions A and B were fit with first-order exponentials. The exponential efflux properties of these regions were compared to the model output for the healthy mice groups.

II. RESULTS

The average pre-infusion Mn content in the heart and blood was found to be 1.13±0.01 and 2.02±0.37 nmoles respectively, assuming a total heart weight of 0.1 g, and a total blood volume of 2.17 ml/25 g BW. Correlating the ex vivo elemental analysis data to in vivo $\Delta R_1$ data allowed for a relationship between the increase in Mn content (above the pre-infusion baseline) and $\Delta R_1$ to be obtained (Eq. [12], $r^2$=0.91). Using this equation, estimates for the increase in absolute Mn content were made from in vivo $\Delta R_1$ values.

$$\text{Increase in Mn content[nmoles]}=11.56 \cdot \Delta R_1 [\text{sec}^{-1}] \quad (12)$$

From Eq. [9], $r_{1,T}$ is therefore equal to 1/11.56 nmoles$^{-1}$ s$^{-1}$.

Figure 7:
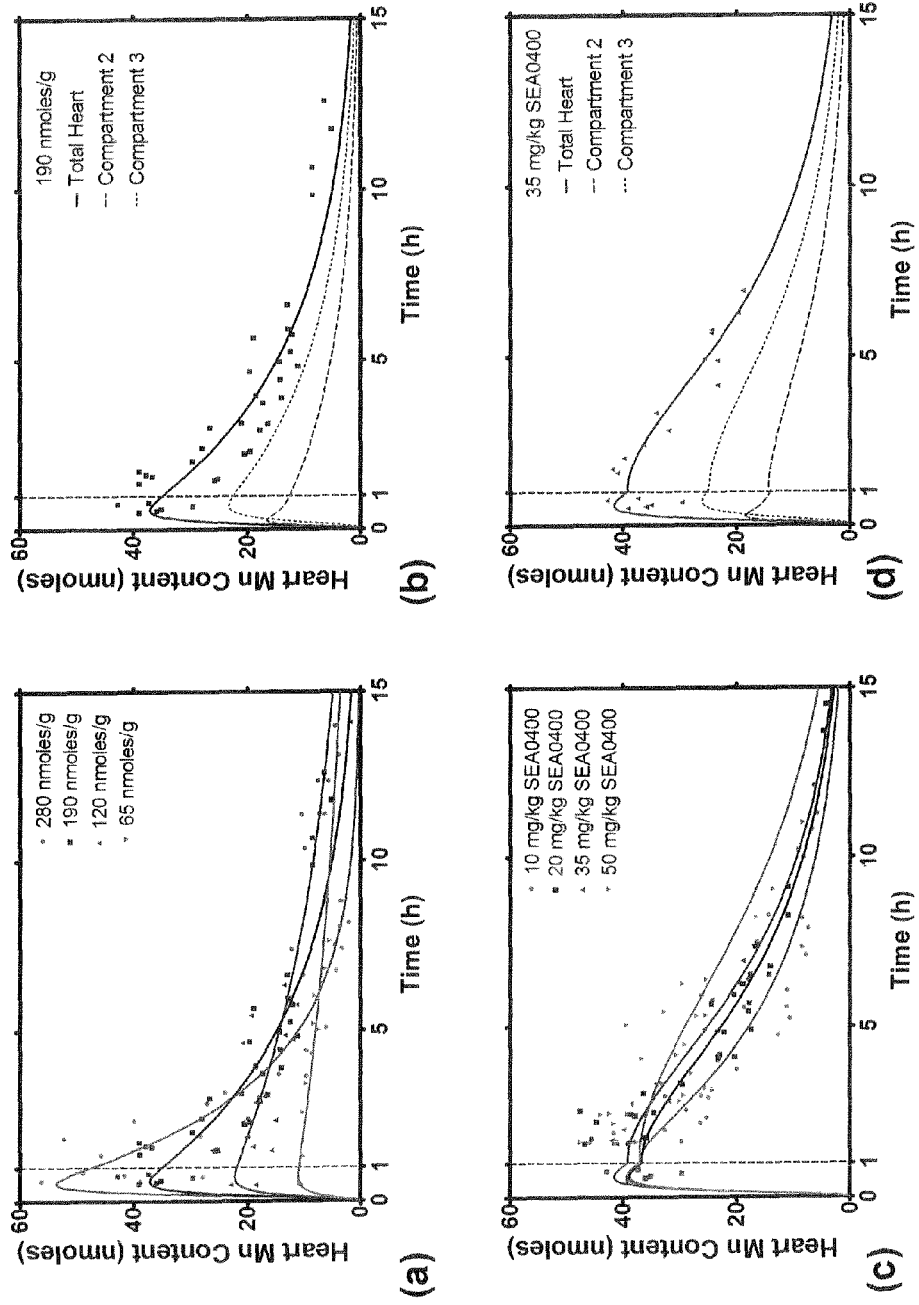
FIG. 7 shows cardiac $Mn^{2+}$ efflux data for the $MnCl_2$ dose dependent infusion groups (a), and the SEA0400 dose dependent groups (c). Overlaid are the least square best fit total heart model results from Model 2. $Mn^{2+}$ content in the heart (compartments 2+3, solid line), compartment 2 (dashed line) and compartment 3 (dotted line) for the 190 nmoles/g $MnCl_2$ and 35 mg/kg SEA0400 groups are shown in (b) and (d) respectively.
Figure 8:
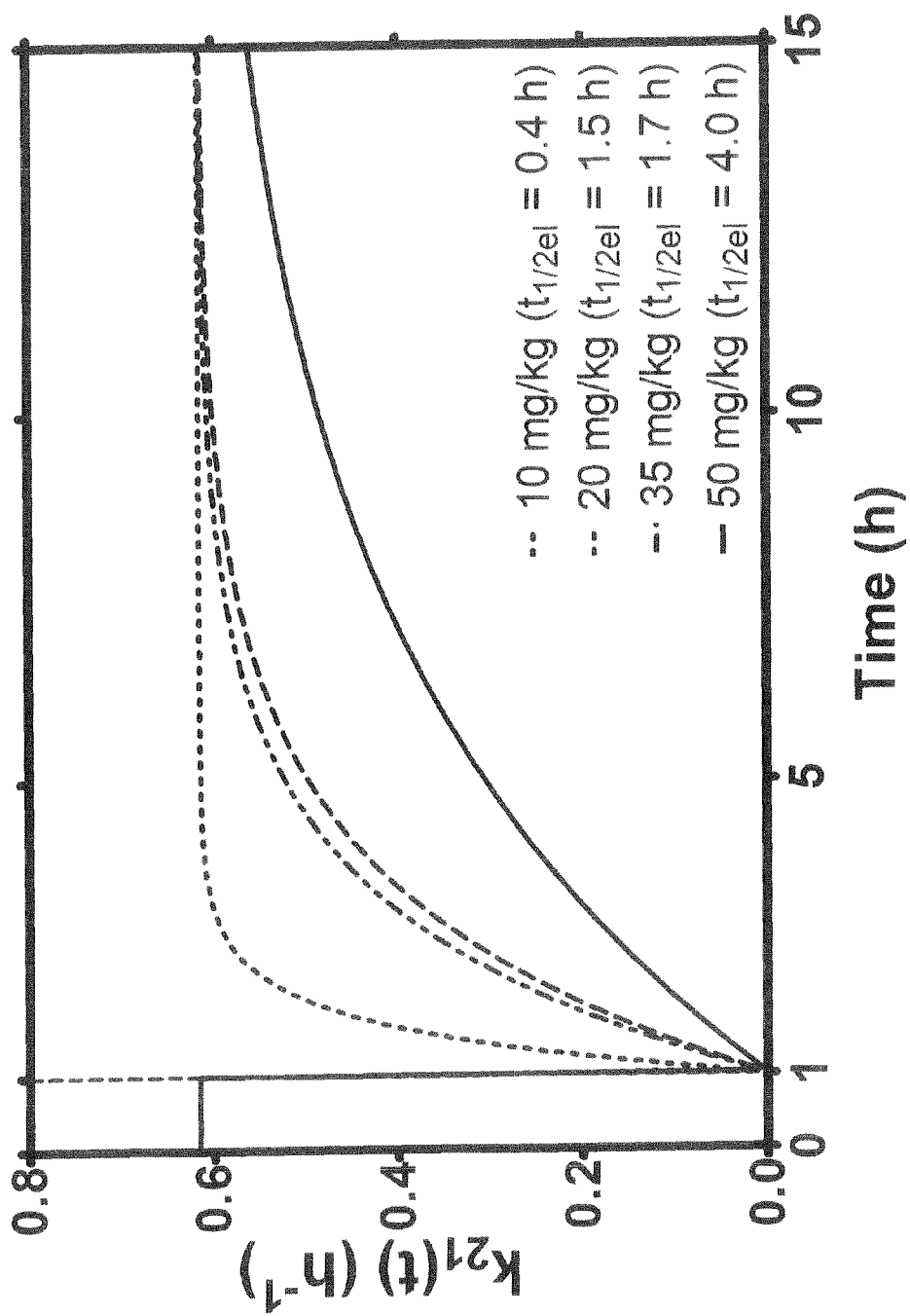
FIG. 8 shows temporal $Mn^{2+}$ efflux transfer rate, $k_{21}(t)$, predicted by Model 2 following inhibition of the NCX with varying does of SEA0400, injected 1 hour post-$MnCl_2$ infusion. Also shown are the corresponding SEA00400 elimination half-lives.
Figure 9:
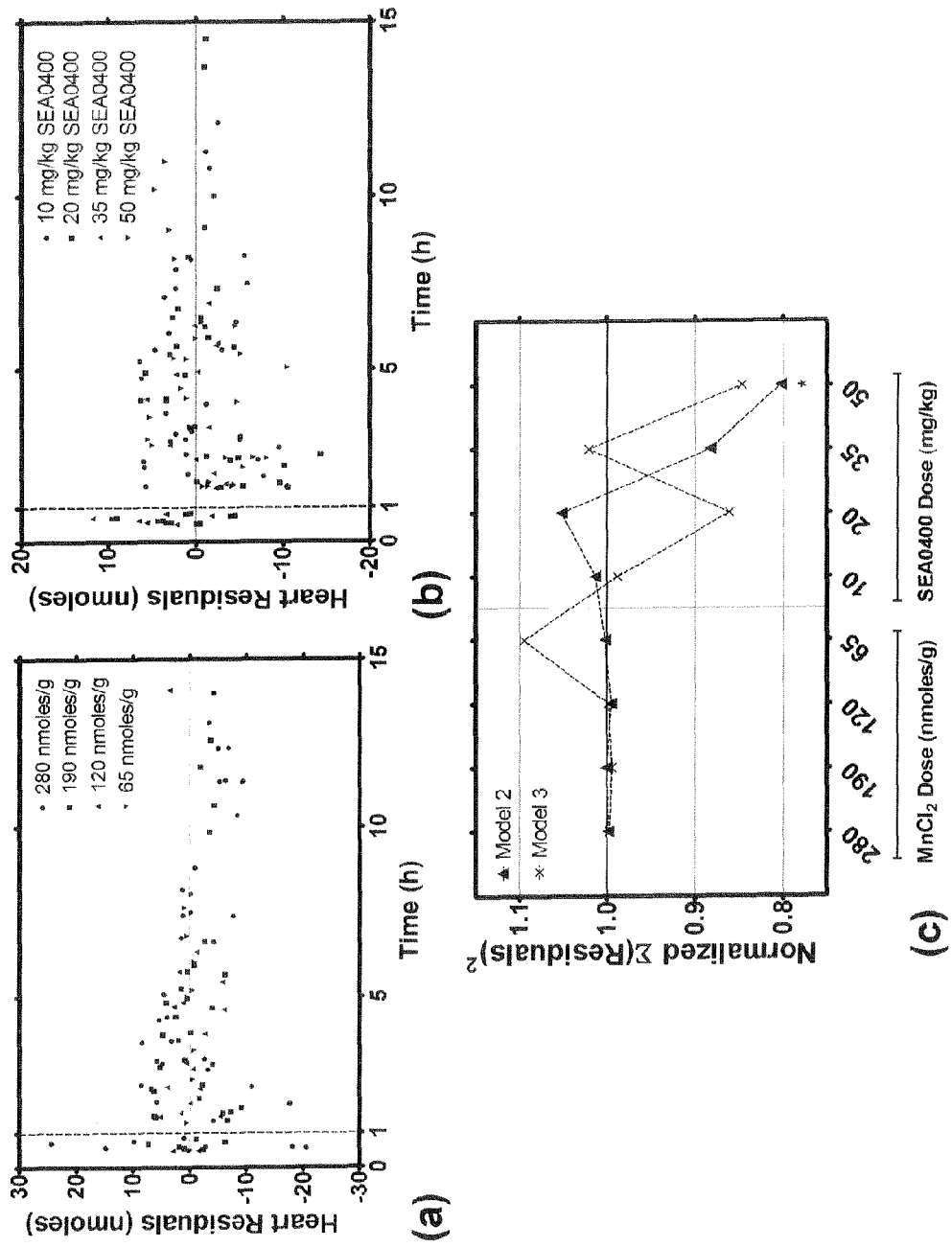
FIG. 9 shows model 2 total heart compartment (compartments 2 and 3) residuals for the control (a) and SEA0400 (b) dose dependent groups c) Model comparisons of the combined blood and heart sum of residuals squared for all the study groups, normalized to Model 1. * represents significance ($p<0.05$)

FIG. 7 shows the raw LV Wall Mn efflux data for the dose dependent (FIG. 7a) and SEA0400 (FIG. 7c) groups, along with the best fit solutions to Model 2 (solid lines). The total Mn$^{2+}$ content in the heart (compartments 2+3, solid line), compartment 2 (dashed line) and compartment 3 (dotted line) for the 190 nmoles/g MnCl$_2$ and 35 mg/kg SEA0400 groups are shown in FIGS. 7b and 7d respectively. The SEA0400 dose dependent temporal fits for $k_{21}$ are shown in FIG. 8, with the temporal residuals for Model 2 displayed in FIGS. 9a and 9b.

Model Comparison

The least-square best-fit parameters from all three models are summarized in Table 3. By definition the SEA0400 groups have the same transfer rate parameters as the 190 nmoles/g MnCl$_2$ group, with the additional pharmaceutical parameters $k_{abs}$ and $k_{el}$ also shown in Table 3. Individual coefficients of determination, $R^2$, are shown in the lower right region of Table 3. For comparison between the three models, FIG. 9c displays the sum of square residuals for the combined blood and heart data, normalized to Model 1, for each of the groups. Using an F test, there was no statistically significant benefit in increasing the number of model variables for each individual efflux group (p>0.05), with the exception of the 50 mg/kg SEA0400 group where Model 2 provided a significant improvement over Model 1 (p=0.02). Considering this, Model 1 provided a simple model which potentially would be adequate fit for dose dependent efflux groups, as well as the 10, 20 and 35 mg/kg SEA0400 groups. The addition of a third compartment in Model 2 created a statistically significant improvement over the two-compartment model for the 50 mg/kg SEA0400 group. It is possible however those models with multi-cardiac compartments could provide more utility and realism in other pathological circumstances. Indeed, since the three-compartment model provided a better description for the 50 mg/kg SEA0400 group, and since there is virtually no difference between the models under other circumstances, use of a three-compartment model provides the most useful description in the current sensitivity of cardiac MEMRI conditions.

The robustness of the different models can also be demonstrated from Table 3. The transfer rate parameters from the smaller, less complicated, models have demonstrated stability following addition of more compartments. FIG. 10 displays the transfer rate parameters and pharmaceutical absorption and elimination half lives for the statistically best models. Applying a linear least square best-fit to the dose dependent transfer rate parameters yielded:

$$k_{10}=(3.9\pm1.4\times10^{-3})\times\text{Dose}+(5.8\pm0.3)(R^2=0.78) \quad (13)$$

$$k_{12}=(1.2\pm0.3\times10^{-4})\times\text{Dose}+(0.04\pm0.01)(R^2=0.90) \quad (14)$$

$$k_{21}=(1.4\pm0.2\times10^{-3})\times\text{Dose}-(0.04\pm0.03)(R^2=0.97) \quad (15)$$

Similarly, first order exponential fits to the SEA0400 half lives yield:

$$t_{1/2abs}[\text{min}]=(4.9\pm7.2\times10^{-3})\times\exp((8.5\pm3.0\times10^{-2})\times\text{Dose})(R^2=0.92) \quad (16)$$

$$t_{1/2el}[\text{hrs}]=(0.30\pm0.17)\times\exp((5.2\pm1.2\times10^{-2})\times\text{Dose})(R^2=0.94) \quad (17)$$

The best fits from Eq. [13] through [17] are displayed in FIGS. 5a and 5b.

Myocardial Infarction

Figure 11:
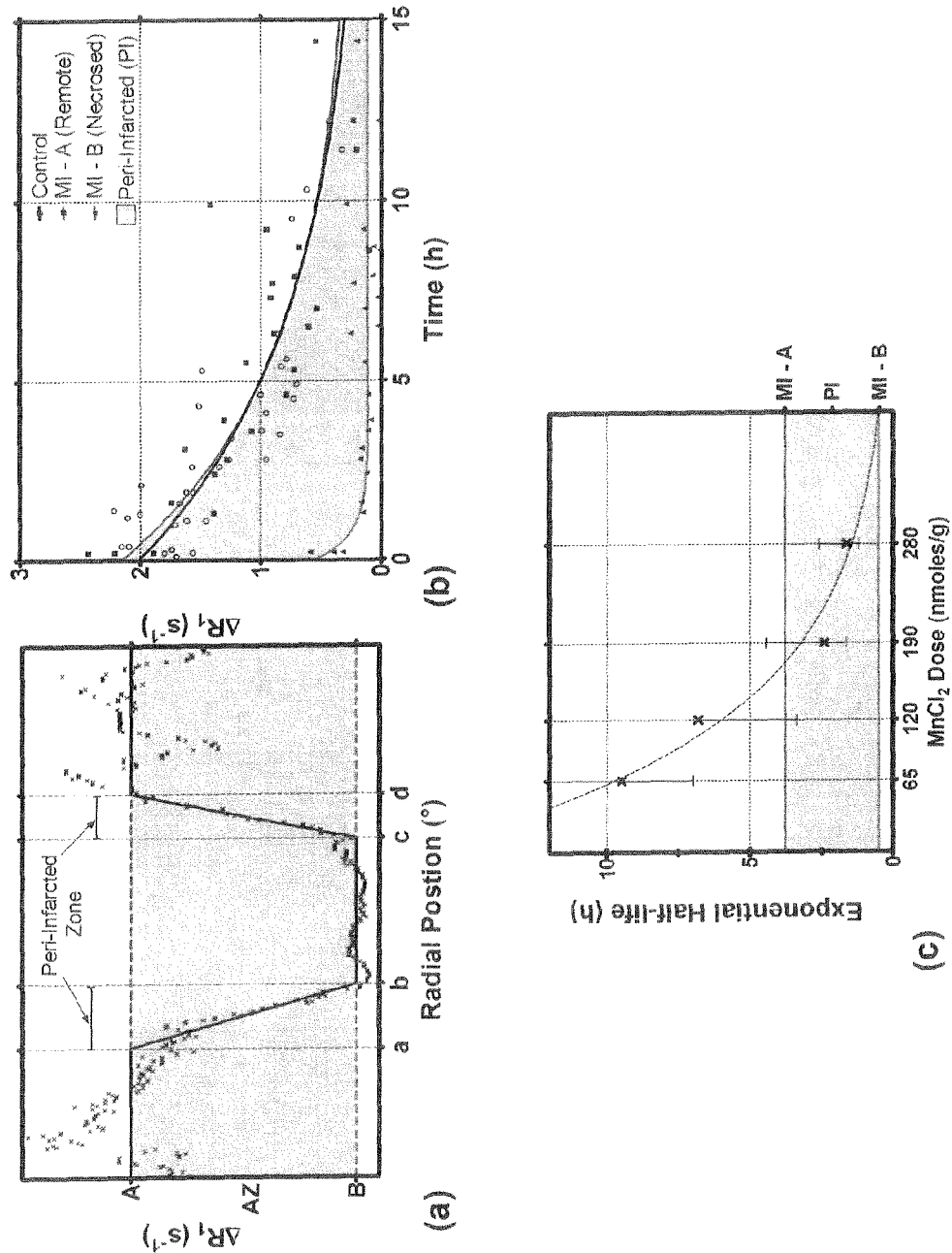
FIG. 11 shows the comparison of the MI efflux data to the modeled healthy efflux data. (a) shows an example output from the radial MI fitting algorithm, fitting constant $\Delta R_1$ values for the remote (A) and necrosed (B) tissue, and linearly changing $\Delta R_1$ in peri-infarcted zone between. The temporal efflux of regions A and B are illustrated in (b). The exponential efflux half-lives for these regions are compared to the healthy, dose dependent efflux in (c). The potentially salvageable peri-infarcted zone tissue is shaded in all three subplots.

Results from the MI study are displayed in FIG. 11. FIG. 11a represents, for one mouse, a sample regional plot of the remote ($\Delta R_1$=A) and necrosed ($\Delta R_1$=B) tissue, as well as the boundaries of the peri-infarcted zone. The range of peri-infarcted zone values is shaded in all the subplots of FIG. 11. FIG. 11b displays the temporal response of Mn$^{2+}$ efflux in regions A and B, with first order exponential fits overlaid. In order to compare the infarcted efflux data to the control dose dependent data, a third plot, FIG. 11c, is shown. This figure displays the efflux half lives of the dose dependent groups, as well as those for regions A and B. Following extrapolation of the exponential fit to the dose dependent half lives, the infarcted region is shown to correspond to a $MnCl_2$ infusion dose of approximately 400 nmoles/g. Using the linear fit for the predicted efflux transfer rate, $k_{21}$ (Eq. [15]), shown in FIG. 10a, the approximate efflux transfer rate for the infarcted region is $0.52\ h^{-1}$, an increase from $0.22\ h^{-1}$ for the viable region of the same infusion dose. The efflux transfer rates for the peri-infarcted zone vary continuously between these limits.

III. DISCUSSION

The goals of this study were to characterize the $Mn^{2+}$ transport properties using pharmacokinetic modeling to gain an insight into the relationship between $Mn^{2+}$ and indirect $Ca^{2+}$ transport in the healthy heart as well as alteration in $Mn^{2+}$ handling following MI. The groups used to study the $Mn^{2+}$ handling properties in the healthy heart were designed to test both the infusion dose dependence on $Mn^{2+}$ influx and efflux, as well as to probe the efflux mechanisms by inhibiting the NCX with varying doses of SEA0400. It was found that, given the current sensitivity of the MEMRI technique, a two-compartment model incorporating compartments for the blood and heart (Model 1), was sufficient to describe the systems of $Mn^{2+}$ transport. Only modeling of the 50 mg/kg SEA0400 group (FIG. 9c), the most extreme case of NCX inhibition, gained a significant improvement with the addition of a third compartment representing cytosolic compartmentalization. These findings suggest that compartmentalization is not negligible; however, prolonged retention of $Mn^{2+}$ is required in order for the models to be able to quantify this with certainty. Indeed, over the experimental timeframe Model 2 predicts that over half of the $Mn^{2+}$ contained within the cytosol is retained within intracellular compartments (FIG. 7).

Within this study, the transfer rate parameters $k_{10}$, $k_{12}$ and $k_{21}$, were all shown to increase linearly with increasing $MnCl_2$ infusion doses (FIG. 10a). The dose dependence of the linear uptake parameter, $k_{12}$, is in agreement with work previously conducted, studying the relationship between $Mn^{2+}$ infusion dose and myocardial $Mn^{2+}$ uptake. While $Mn^{2+}$ is known to act as a surrogate marker for $Ca^{2+}$ with respect to ionic uptake and efflux from the cytosol, the relationship between $Ca^{2+}$ transport and $Mn^{2+}$ transport is not well known. The relative contributions of the NCX and PMCA are likely to be different for $Mn^{2+}$ and $Ca^{2+}$ due to differences between their binding constants. Similarly, low extracellular $Mn^{2+}$ concentrations create a concentration gradient potentially allowing $Mn^{2+}$ extrusion to occur via the $Ca^{2+}$ channels, while intracellular compartmentalization may also differ between the ions.

For $Ca^{2+}$, the NCX is known to account for approximately 80% of the total efflux in mice. Model 2 predicts that following inhibition of the NCX, the $Mn^{2+}$ efflux rate is reduced to just 8.2, 1.8, 1.6 and 1.0% of the initial, pre-SEA0400 administration, rate for the 10, 20, 35 and 50 mg/kg SEA0400 groups respectively. This maximum inhibition occurred on average 3 minutes post-SEA0400 administration. A possible cause of the difference between $Ca^{2+}$ and $Mn^{2+}$ efflux is due to the aforementioned differences in the extracellular concentrations of the respective ions. The relative contribution from the passive NCX is expected to increase with decreasing ion concentration gradients, with a consequent reduction in the contributions from the active PMCA. This effect is observed following inhibition of the NCX, where for the highest dose of SEA0400 the models predict that approximately 99% of $Mn^{2+}$ efflux occurs via the NCX.

With respect to compartmentalization, it has been shown that $Ca^{2+}$ uptake into the SR and mitochondria occurs at rates of $6.1\times10^{-3}$ and $1.0\times10^{-6}\ M\ s^{-1}$, respectively, compared to an efflux rate of $3.0\times10^{-2}\ M\ s^{-1}$ across the NCX. The efflux rate for $Ca^{2+}$ is therefore approximately 5 times greater than for compartmentalization. In contrast, Model 2 predicts that the uptake of $Mn^{2+}$ into the intracellular compartments occurs at a rate approximately 12 times greater than the efflux rate. Although further studies are required to fully address this potential effect, if found to be significant, differences in $Mn^{2+}$ and $Ca^{2+}$ handling could potentially be explained by differences in the binding constants of the ions.

Model 3 attempts to address differences in relaxivity between free cytosolic $Mn^{2+}$ and compartmentalized $Mn^{2+}$. For the dose dependent groups, the relaxivity of the compartments (SR and mitochondria) was found to be $2.3\pm0.1$ times larger than for free cytosolic $Mn^{2+}$. This is most likely caused by the binding of $Mn^{2+}$ to larger molecules within the compartments. An alternative hypothesis would be that, once compartmentalized, $Mn^{2+}$ becomes chelated, thus reducing the relaxivity; however this effect was not predicted by the models. When considering the contribution of multiple compartments on the overall relaxation rate, a more thorough representation of the effective relaxation rate would be to consider the be the weighted average of the relaxation in the two compartments. If compartment i has a volume fraction $f_i$, an initial $T_1$ given by $T_{1i}$ and a contrast agent concentration $C_i$, then the effective relaxation rate is given by Eq. [18].

$$\frac{1}{T_1} = \sum_i f_i \left( \frac{1}{T_{1i}} + r_{1i} C_i \right) \quad (18)$$

Model 3 incorporates a simplification of this equation (Eq. [9]), assuming that the volume fractions, $f_i$, for the free $Mn^{2+}$ and compartmentalized $Mn^{2+}$ are equal to each other. While a reasonable approximation for this study, the cytosol only constitutes approximately 11.5% of the myocardial cell volume, with the SR and mitochondria accounting for 36% and 3.5% respectively.

The pharmacokinetic properties of SEA0400 were also addresses in this study, assuming that the plasma concentration was inversely proportional to the efflux rate, $k_{21}$ (Eq. [3]). The models all predict that the drug uptake occurs rapidly, with the maximum inhibition of the NCX occurring approximately 3 minutes post-administration. With respect to drug elimination, the predicted SEA0400 elimination half-lives are predicted to be of the same order of magnitude as unpublished SEA0400 data in rats. Although there is no published data for the kinetic properties of SEA0400, the assumptions and models presented in this current study appear to provide a good first order approximation for the pharmacokinetic transport properties of SEA0400, although further work is warranted to fully understand this.

It has previously been demonstrated that $T_1$-mapping MEMRI can be used to delineate different regions of the infarcted myocardium. This current study provides additional information with regards $Mn^{2+}$ handling within different regions of the infarcted myocardium. FIG. 11c demonstrates that the $Mn^{2+}$ efflux half-life of the necrotic tissue within the MI site, as well as the peri-infarcted zone tissue, corresponds to efflux half-lives observed following increased $Mn^{2+}$ infusion doses in healthy mice. The affected tissue also has $Mn^{2+}$ handling properties associated with increased $Mn^{2+}$ efflux rates. Application of MEMRI techniques to detect increases in indirect $[Ca^{2+}]_i$, in ischemic tissue are currently limited, in part due to reduced perfusion in the ischemic tissue. However, by modeling $Mn^{2+}$ efflux data, this study has demonstrated the ability of MEMRI $T_1$-mapping to minimize the uncertainties caused by perfusion limitations. The technique has also indirectly predicted an increase in $Mn^{2+}$ efflux rates with relative increased $Mn^{2+}$ content proximally to NCX and PMCA in the viable cells within ischemic regions. This increase is consistent with ex vivo $Ca^{2+}$ studies, with the MEMRI $T_1$-mapping efflux technique having the potential to be used to indirectly predict alterations in $Ca^{2+}$ handling in the infarcted heart.

IV. CONCLUSIONS

Implementation of three multi-compartment pharmacokinetic models to $Mn^{2+}$ efflux data in healthy and infarcted mice hearts has been demonstrated to effectively model $Mn^{2+}$ transport mechanisms. In order to address the difference in $Mn^{2+}$ and $Ca^{2+}$ handling in the myocardium, the model predicted that $Mn^{2+}$ is more dependent on the NCX for ionic efflux than is $Ca^{2+}$. This is likely due to the difference in the concentration gradients between the ions, driving the passive NCX pump. Within the cytosol the model predicts that $Mn^{2+}$ uptake into compartments occurs at a faster rate than for efflux, contrary to the effect observed for $Ca^{2+}$. This can potentially be explained by considering differences in the binding constants for $Mn^{2+}$ and $Ca^{2+}$. Additionally, $Mn^{2+}$ stored within intracellular compartments, for example the SR and mitochondria, exhibits an apparent increase in relaxivity, $r_1$, relative to free cytosolic $Mn^{2+}$, possibly due to $Mn^{2+}$ binding with larger molecules.

Finally, there is an apparent increase in the $Mn^{2+}$ efflux rate from ischemic tissue, commensurate with increased $Mn^{2+}$ content in viable cells within these regions. This effect has been widely observed for ex vivo $Ca^{2+}$ transport, but has thus far proved elusive for in vivo MEMRI studies. The predictions made by this modeling technique allow for a more thorough understanding of the relationship between $Mn^{2+}$ and $Ca^{2+}$ handling in the heart. This approach therefore has the potential to be applied as a diagnostic tool in the early detection of abnormal $Ca^{2+}$ handling in the myocardium, and for monitoring disease progression.

While the invention has been described with reference to preferred and example embodiments, it will be understood by those skilled in the art that a variety of modifications, additions and deletions are within the scope of the invention, as defined by the following claims.

Tables

TABLE 1

Summarized raw input data

| Study Group | Infusion Time, T (h) | Number of mice | Number of $T_1$-Maps | Number of blood data points |
|---|---|---|---|---|
| Control (nmoles/g $MnCl_2$) | | | | |
| 283 ± 6 | 0.18 | 14 | 41 | 3 |
| 190 ± 2 | 0.12 | 14 | 36 | 9 |
| 119 ± 3 | 0.08 | 7 | 21 | 1 |
| 65 ± 0.2 | 0.05 | 4 | 14 | 1 |
| SEA0400 (mg/kg) (1 h post-190 nmoles/g BW $MnCl_2$) | | | | |
| 10 ± 0.2 | 0.13 | 11 | 35 | 1 |
| 20 ± 0.2 | 0.13 | 8 | 33 | 1 |
| 34 ± 0.8 | 0.14 | 4 | 17 | 1 |
| 50 ± 0.2 | 0.13 | 7 | 29 | 9 |
| Myocardial Infarction (nmoles/g $MnCl_2$) | | | | |
| 190 ± 1 | 0.13 | 9 | 30 | — |

TABLE 2

Summary of the pharmacokinetic models

| | Compartment | | | | Efflux | Model Fit Parameters | Total |
|---|---|---|---|---|---|---|---|
| Model | 1 | 2 | 3 | 4 | Group | Parameter | Number |
| 1 | Blood | Total Myocardium | — | — | $MnCl_2$<br>SEA0400 | $k_{10}, k_{12}, k_{21}$<br>$k_{abs}, k_{el}$ | 5 |
| 2 | Blood | Free Cytosol | Cytosolic Compartments | — | $MnCl_2$<br>SEA0400 | $k_{10}, k_{12}, k_{21}, k_{23}, k_{32}$<br>$k_{abs}, k_{el}$ | 7 |
| 3 | Blood | Free Cytosol | Sarcoplasmic Reticulum | Mitochondria | $MnCl_2$ and SEA0400 | $k_{10}, k_{12}, k_{21a,21b}$ (NCX, PMCA), $k_{23,24} k_{32}, k_{42}$, a, b, $k_{abs}, k_{el}$ | 10 |

TABLE 3

Best fit parameters calculated by the three models

| Dose Control (nmoles/g) | Model Fit Parameters (Model 1/Model 2/Model 3) Transfer rate parameters (h⁻¹) | | | | | | | Model 3 (s⁻¹nmoles⁻¹) |
| --- | --- | --- | --- | --- | --- | --- | --- | --- |
| | $k_{10}$ | $k_{12}$ | $k_{21(a,)}$ | $k_{23}$ | $k_{32}$ | $k_{24}$ | $k_{42}$ | a/b (×11.56) |
| 280 | 6.9/6.9/6.9 | 0.07/0.07/0.07 | 0.37/0.91/0.79 | —/5.9/0.41 | —/4.5/0.57 | —/—/0.05 | —/—/0.87 | 1.1/2.3 |
| 190 | 6.4/6.7/6.6 | 0.06/0.06/0.06 | 0.22/0.62/0.71 | —/7.4/0.48 | —/4.3/0.37 | —/—/0.05 | —/—/0.75 | 1.1/2.4 |
| 119 | 6.5/6.1/6.5 | 0.06/0.05/0.05 | 0.11/0.54/0.58 | —/11.8/0.61 | —/3.1/0.28 | —/—/0.07 | —/—/0.37 | 1.0/2.5 |
| 65 | 5.9/6.0/6.0 | 0.04/0.04/0.04 | 0.08/0.51/0.60 | —/12.4/0.60 | —/2.4/0.19 | —/—/0.07 | —/—/0.31 | 0.9/2.3 |

| SEA0400 (mg/kg) | Drug Parameters (h⁻¹) | | Coefficient of Determination, $R^2$ | | | |
| --- | --- | --- | --- | --- | --- | --- |
| | $k_{abs}$ | $k_{el}$ | Control (nmoles/g) | | SEA0400 (mg/kg) | |
| 10 | 671/68/85 | 1.7/1.6/1.1 | 280 | 0.83/0.83/0.83 | 10 | 0.86/0.86/0.86 |
| 20 | 672/149/118 | 0.51/0.47/0.44 | 190 | 0.83/0.83/0.83 | 20 | 0.86/0.86/0.87 |
| 34 | 680/115/9.4 | 0.49/0.41/0.33 | 119 | 0.80/0.81/0.81 | 34 | 0.87/0.87/0.87 |
| 50 | 66/118/149 | 0.14/0.17/0.06 | 65 | 0.98/0.98/0.98 | 50 | 0.81/0.83/0.83 |

What is claimed is:

1. A method for detecting a change in manganese ion efflux from an organ in a subject, the method comprising:
   a. imaging the organ of the subject to obtain a baseline concentration of manganese ions in the organ;
   b. administering to the subject a known concentration of a source of manganese ions;
   c. imaging the organ of the subject after step (b) to obtain the concentration of manganese ions;
   d. comparing the manganese ion concentration from step (c) to a standard multi-compartment pharmacokinetic model of a healthy organ at the same manganese ion concentration in step (b), wherein a deviation from the standard multi-compartment pharmacokinetic model indicates a change in manganese ion efflux from the organ.

2. The method of claim 1, wherein the organ is imaged by an MRI machine.

3. The method of claim 1, wherein the organ is imaged by a MRI mapping technique, a manganese-enhanced MRI (MEMRI) mapping technique, or a combination thereof.

4. The method of claim 1, wherein step (c) comprises use of temporal $\Delta R_1$ values to determine the manganese ion concentration over time.

5. The method of claim 1, wherein the organ is imaged to produce a segmented radial $T_1$ map.

6. The method of claim 1, wherein the source of manganese ions is $MnCl_2$, manganese dipyridoxyl diphosphate (MnDPDP), or manganese gluconate/calcium gluconate.

7. The method of claim 1, wherein the organ is imaged from 1 to 6 times over a period of 30 minutes to 9 hours after step (b).

8. The method of claim 1, wherein the organ is a heart, brain, liver, kidney, pancreas, bladder, or spine.

9. The method of claim 1, wherein the standard multi-compartment pharmacokinetic model measures the rate of manganese ion efflux from two or more compartments present in the organ.

10. The method of claim 9, wherein the organ is a heart and the compartments comprise a cardiac compartment, a mitochondrion, sarcoplasmic reticulum, or any combination thereof.

11. The method of claim 9, wherein the standard multi-compartment pharmacokinetic model comprises a blood compartment and a heart compartment.

12. The method of claim 1, wherein the change in manganese ion efflux is due to an ischemic or arrhythmia event.

13. The method of claim 12, wherein the ischemic event is a myocardial event.

14. The method of claim 13, wherein the myocardial event comprises heart palpitations, a myocardial infarction, chest pain, shortness of breath, nausea, vomiting, sweating, anxiety, fatigue, heart attack, cardiac arrest, heart failure, or any combination thereof.

15. The method of claim 1, further comprising quantifying the change in manganese ion efflux from the organ of the subject.

16. The method of claim 1, wherein the method detects a change in manganese ion efflux and influx from the organ in the subject.

17. A non-transitory computer-readable medium storing instructions that, when executed on a programmed processor, carry out a method for detecting and quantifying a change in manganese ion efflux from an organ, wherein the method comprises:
   a. obtaining a baseline concentration of manganese ions in the organ after the organ has been imaged and prior to administration of a known concentration of a source of manganese ions to a subject;
   b. obtaining the concentration of manganese ions in the organ by imaging the agent at a specific time after administration of the known concentration of a source of manganese ions to the subject;
   c. comparing the manganese ion concentration from step (b) to a standard multi-compartment pharmacokinetic model of a healthy organ administered the same concentration of the source of manganese ions, wherein a deviation from the standard multi-compartment pharmacokinetic model indicates a change in manganese ion efflux from the organ; and
   d. quantifying a change in manganese ion efflux from the organ.

18. A non-transitory computer-readable medium of claim 17, wherein the method further comprises producing a segmented radial $T_1$ map.

19. The non-transitory computer-readable medium of claim 17, wherein when executed on a programmed processor, carries out a method for detecting and quantifying a change in manganese ion efflux and influx from the organ in the subject.

20. A computer system for detecting and quantifying a change in manganese ion efflux from an organ, comprising:
   a. a baseline module for obtaining a baseline concentration of manganese ions in the organ after the organ has been imaged and prior to administration of a known concentration of a source of manganese ions to a subject;
   b. a concentration module for obtaining the concentration of manganese ions in the organ by imaging the agent at a specific time after administration of the known concentration of a source of manganese ions to the subject;
   c. a comparison module for comparing the manganese ion concentration from step (b) to a standard multi-compartment pharmacokinetic model of a healthy organ administered the same concentration of the source of manganese ions, wherein a deviation from the standard multi-compartment pharmacokinetic model indicates a change in manganese ion efflux from the organ;
   d. a calculating module for quantifying a change in manganese ion efflux from the organ; and
   e. a map module that produces a segmented radial T1 map.

21. The system of claim 20, wherein the system detects and quantifies the change in manganese ion efflux and influx from the organ in the subject.

\* \* \* \* \*